United States Patent
Lee

(10) Patent No.: US 9,907,857 B2
(45) Date of Patent: Mar. 6, 2018

(54) PEPTIDE HAVING CELL MEMBRANE PENETRATING ACTIVITY

(71) Applicant: EWHA UNIVERSITY-INDUSTRY COLLABORATION FOUNDATION, Seoul (KR)

(72) Inventor: Kyunglim Lee, Seoul (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 15/141,731

(22) Filed: Apr. 28, 2016

(65) Prior Publication Data

US 2016/0324976 A1    Nov. 10, 2016

Related U.S. Application Data

(60) Division of application No. 13/669,414, filed on Nov. 5, 2012, now abandoned, which is a continuation of application No. 12/280,077, filed as application No. PCT/KR2007/000885 on Feb. 20, 2007, now abandoned.

(30) Foreign Application Priority Data

Feb. 20, 2006 (KR) ........................ 10-2006-0016156

(51) Int. Cl.

| | |
|---|---|
| A61K 47/64 | (2017.01) |
| A61K 47/48 | (2006.01) |
| C07K 7/06 | (2006.01) |
| C07K 14/47 | (2006.01) |
| C07K 14/435 | (2006.01) |
| C07K 16/18 | (2006.01) |
| C07K 7/08 | (2006.01) |
| A61K 48/00 | (2006.01) |
| C07K 14/46 | (2006.01) |
| A61K 47/65 | (2017.01) |

(52) U.S. Cl.
CPC ........ *A61K 47/48246* (2013.01); *A61K 47/64* (2017.08); *A61K 47/65* (2017.08); *A61K 48/0008* (2013.01); *C07K 7/06* (2013.01); *C07K 7/08* (2013.01); *C07K 14/435* (2013.01); *C07K 14/46* (2013.01); *C07K 14/47* (2013.01); *C07K 16/18* (2013.01)

(58) Field of Classification Search
None
See application file for complete search history.

(56) References Cited

U.S. PATENT DOCUMENTS

| | | | |
|---|---|---|---|
| 6,468,537 B1 | 10/2002 | Datta et al. | 424/185.1 |
| 6,710,165 B2 | 3/2004 | Lee et al. | 530/300 |
| 6,835,810 B2 | 12/2004 | Hwu | 435/69.7 |
| 7,772,368 B2 | 8/2010 | Lee et al. | 530/350 |
| 2002/0095023 A1 | 7/2002 | Lee et al. | 530/350 |
| 2002/0177692 A1 | 11/2002 | Bartel et al. | 435/184 |
| 2004/0072341 A1 | 4/2004 | Katinger et al. | 435/325 |
| 2004/0087531 A1 | 5/2004 | Telerman et al. | 514/44 |
| 2005/0202069 A1 | 9/2005 | Kurokawa et al. | 514/2 |
| 2005/0221303 A1 | 10/2005 | Telerman et al. | 435/184 |
| 2005/0282281 A1 | 12/2005 | Paik et al. | 435/320.1 |
| 2006/0165677 A1 | 7/2006 | Lee et al. | 424/131.1 |
| 2013/0129726 A1 | 5/2013 | Lee | 424/134.1 |
| 2013/0136742 A1 | 5/2013 | Lee et al. | 424/134.1 |

FOREIGN PATENT DOCUMENTS

| | | |
|---|---|---|
| EP | 0 838 472 | 6/1996 |
| EP | 1 167 526 | 1/2002 |
| JP | 2002-330772 | 11/2002 |
| KR | 10-2001-0001269 | 6/1999 |
| KR | 10-0457350 | 11/2004 |
| WO | WO 1998/11125 | 3/1998 |
| WO | WO 2003/040165 | 5/2003 |

OTHER PUBLICATIONS

Letter/Written Disclosure of the Information Disclosure Statement for the above-referenced application, filed herewith on Jul. 28, 2016, 2 pages.
Antoine et al., "Direct Probing of Zwitterion Formation in Unsolvated Peptides," J. Am. Chem. Soc. 125:8996-8997 (2003).
Arcuri et al., "Translationally controlled tumor protein (TCTP) in the human prostate and prostate cancer cells: Expression, distribution, and calcium binding activity," The Prostate 60 (2):130-140 (2004).
Atlas, D., "The Active Site of Porcine Elastase," J. Mol. Biol. 93:39-53 (1975).
Bachran, C. et al., "Influence of Protein Transduction Domains on Target-Specific Chimeric Proteins," Biochemical and Biophysical Research Communications 337:602-609 (2005).
Bae et al., "On employing a translationally controlled tumor protein-derived protein transduction domain analog for transmucosal delivery of drugs." J. Control Release Jun. 17, 2013. pii: S0168-3659(13)00344-1. doi: 10.1016/j.jconrel.2013.06.010. [Epub ahead of print].
Bae et al., "Translationally controlled tumor protein induces epithelial to mesenchymal transition and promotes cell migration, invasion and metastasis." Sci Rep. 5:8061 (2015).
Böhm et al., "The growth-related protein P23 of the Ehrlich ascites tumor: translational control, cloning and primary structure." Biochem Int. 19(2):277-286 (1989).
Casella et al., "Haem-peptide complexes. Synthesis and stereoselective oxidation by deuterohaemin-1-phenylalanyl-poly-1-alanine complexes" J Chem Soc Dalton Trans (14): 2233-2239 (1993).
Chitpatima et al., "Nucleotide sequence of a major messenger RNA for a 21 kilodalton polypeptide that is under translational control in mouse tumor cells." Nucleic Acids Res. 16:2350 (1988).
Choi et al., "Proton pump inhibitors exert anti-allergic effects by reducing TCTP secretion." PLoS One 4(6):e5732 (2009).

(Continued)

*Primary Examiner* — Karlheinz R. Skowronek
*Assistant Examiner* — Ronald T Niebauer
(74) *Attorney, Agent, or Firm* — Dentons US LLP; Stephanie Seidman

(57) ABSTRACT

Provided are transmembrane complexes that contain a protein transduction domain (PTD) from the N-terminus of IgE-dependent histamine-releasing factor (HRF) and a target substance that is to be delivered into a cell. Also provided are nucleic acid molecules encoding the transmembrane complex and methods of delivering the target substance into a cell interior by contacting the transmembrane complex with a cell. Also provided are transfection kits containing the PTD and the target substance.

3 Claims, 11 Drawing Sheets

(56) References Cited

OTHER PUBLICATIONS

Choi, et al., "Intranasal delivery of the cytoplasmic domain of CTLA-4 using a novel protein transduction domain prevents allergic inflammation," Nature Medicine, 12(5):574-9 (2006).
Elliot et al., "Intercellular trafficking and protein delivery by a herpesvirus structural protein." Cell 88(2):223-233 (1997).
Frankel et al., "Cellular uptake of the tat protein from human immunodeficiency virus." Cell 55(6):1189-1193 (1988).
Futaki, S., "Intracellular Delivery of Biopolymers Using Membrane-Permeable Peptides," Membrane, 28(2): 55-60, (2003), with English abstract.
Futaki, S., "Intracellular Protein Delivery Using Membrane-Permeable Peptides," Journal of Biology and Chemistry, 43(10): 649-653 (2005), with English abstract.
Gachet et al., "The growth-related, translationally controlled protein P23 has properties of a tubulin binding protein and associates transiently with microtubules during the cell cycle." J. Cell Sci. 112: 1257-1271 (1999).
Green et al., "Autonomous functional domains of chemically synthesized human immunodeficiency virus tat trans-activator protein." Cell 55(6): 1179-1188 (1988).
Hoffman et al., "Stimulation of human and murine adherent cells by bacterial lipoprotein and synthetic lipopeptide analogues." Immunobiology, 177(2):158-170 (1988).
Joliot et al., "Antennapedia homeobox peptide regulates neural morphogenesis." Proc. Natl. Acad. Sci. USA, 88(5):1864-1868 (1991).
Jung et al., "Translationally controlled tumor protein interacts with the third cytoplasmic domain of Na,K-ATPase alpha subunit and inhibits the pump activity in HeLa cells." J Biol Chem. 279(48):49868-49875 (2004).
Kennerknecht et al., "Export of l-isoleucine from Corynebacterium glutamicum: a two-gene-encoded member of a new translocator family," J Bacteriol. Jul. 2002;184(14):3947-56.
Kim et al., "Cellular uptake mechanism of TCTP-PTD in human lung carcinoma cells." Mol Pharm. 12(1):194-203 (2015).
Kim et al. "Dimerization of translationally controlled tumor protein is essential for its cytokine-like activity." PLoS One 4(7): e6464 (2009).
Kim et al., "A peptide binding to dimerized translationally controlled tumor protein modulates allergic reactions." Journal of Molecular Medicine 89(6):603-610 (2011).
Kim et al., "A protein transduction domain located at the NH 2-terminus of human translationally controlled tumor protein for delivery of active molecules to cells." Biomaterials 32:222-230 (2011).
Kim et al., "Design and evaluation of variants of the protein transduction domain originated from translationally controlled tumor protein." Eur J Pharm Sci. 43(1-2):25-31 (2011).
Kim et al., "Dimerization of TCTP and its clinical implications for allergy." Biochimie. 95(4):659-666 (2013).
Kim et al., "Identification of the calcium binding sites in translationally controlled tumor protein." Archives of Pharmacal Research 23(6):633-636 (2000).
Kim et al., "The cell penetrating ability of the proapoptotic peptide, KLAKLAKKLAKLAK fused to the N-terminal protein transduction domain of translationally controlled tumor protein, MIIYRDLISH." Biomaterials 32:5262-5268 (2011).
Leamon et al, "Delivery of macromolecules into living cells: a method that exploits folate receptor endocytosis." Proc Natl Acad Sci USA, 88(13):5572-5576 (1991).
Lee et al., "Neuroprotective effect of Cu,Zn-superoxide dismutase fused to a TCTP-derived protein transduction domain" Eur J Pharmacol. 666(1-3):87-92 (2011).
Li et al., "C-terminal Amino Acid Residue Loss for Deprotonated Peptide Ions Containing Glutamic Acid, Aspartic Acid, or Serine Residues at the C-terminus," J. of Mass Spectrometry, 41:939-949 (2006).
Lopes, L.B. et al., "Comparative Study of the Skin Penetration of Protein Transduction Domains and a Conjugated Peptide," Pharmaceutical Research, 22(5):750-757 (2005).
MacDonald, S. et al.: "Molecular Identification of en IgE-Dependent Histamine-Releasing Factor," Science, 269 (5224): 688-690 (1995).
Machine translation of Korean Patent Publication No. KR2001-0001269 (Korean Patent No. 10-0324549) obtained from KIPO, accessed from http://kposd.kipo.go.kr:8088/up/kpion/ on Nov. 17, 2011, 25 pages.
Maeng et al., "Insulin Induces Phosphorylation of Serine Residues of Translationally Controlled Tumor Protein in 293T Cells." Int J Mol Sci. 16(4):7565-7576 (2015).
Maeng et al., "On the Mechanisms Underlying the Secretion and Export of Translationally Controlled Tumor Protein/Histamine Releasing Factor (TCTP/HRF)." Open Allergy Journal 5:33-40 (2012).
Maeng et al., "Transduction of translationally controlled tumor protein employing TCTP-derived protein transduction domain," Anal Biochem. 35(1):47-53 (2013).
Morris, et al.: "A peptide carrier for the delivery of biologically active proteins into mammalian cells," Nature Biotechnology,19(12):1173-6 (2001).
Nagahara et al., "Transduction of full-length TAT fusion proteins into mammalian cells: TAT-p27Kip1 induces cell migration." Nat Med. 4(12):1449-1452 (1998).
NCBI Protein P13693 [retrieved online on Aug. 16, 2012 from the internet www.ncbi.nlm.nih.govproteinP13693].
Osmotik, (Osmotik web entry retrieved from http://www.osmotik.com/info/membranes.html on Apr. 30, 2012 1 page).
Schroeder et al., "An immunoglobulin E-dependent recombinant histamine-releasing factor induces interleukin-4 secretion from human basophils." J Exp Med. 183(3):1265-1270 (1996).
Schroeder et al., "Recombinant histamine-releasing factor enhances IgE-dependent IL-4 and IL-13 secretion by human basophils." J Immunol. 159(1):447-452 (1997).
Schwarze, et al. "In Vivo Protein Transduction: Delivery of a Biologically Active Protein into the Mouse," Science 285(5433):1569-72 (1999).
Shen, et al., "Conjugation of Poly-L-Lysine Albumin and Horseradish Peroxidase: A Novel Method of Enhancing the Cellular Uptake of Proteins." Proc. Natl. Acad. Sci. USA, 75:1872-1876 (1978).
Sheverdin et al., "Expression and localization of translationally controlled tumor protein in rat urinary organs," Microsc Res Tech. 75(11):1576-81, (2012).
Sheverdin et al., "Immunohistochemical localization of translationally controlled tumor protein in the mouse digestive system." J Anat. 223(3):278-288 (2013).
Thaw et al., "Structure of TCTP reveals unexpected relationship with guanine nucleotide-free chaperones." Nat Struct Biol. 8(8):701-704 (2001).
Thomas et al. "Transcriptional and translational control of cytoplasmic proteins after serum stimulation of quiescent Swiss 3T3 cells." Proc. Natl. Acad. Sci. USA 78:5712-5716 (1981).
Thomas et al., "Translational control of mRNA expression during the early mitogenic response in Swiss mouse 3T3 cells: identification of specific proteins." J Cell Biol. 103(6 Pt 1):2137-2144 (1986).
Uniprot entry G5AS36 [retrieved online on Jan. 25, 2015 from the internet http://uniprot.org/uniprot/G5AS36], 4 pages.
Weinkauf, et al., "Nonstationary Electronic States and Site-Selective Reactivity," J. Phys. Chem. A 101:7702-7710 (1997).
Yang et al., "An N-terminal region of translationally controlled tumor protein is required for its antiapoptotic activity." Oncogene 24:4778-4788 (2005).
International Search Report, dated Jun. 25, 2007, in connection with corresponding International Application No. PCT/KR2007/000885, 4 pages.
Written Opinion, dated Jun. 25, 2007, in connection with corresponding International Application No. PCT/KR2007/000885, 5 pages.

(56) References Cited

OTHER PUBLICATIONS

International Preliminary Report on Patentability, dated Aug. 26, 2008, in connection with corresponding International Application No. PCT/KR2007/000885, 6 pages.
Extended European Search Report and Written Opinion, dated Mar. 6, 2009, in connection with corresponding European Application No. 07 709 034.8, 8 pages.
Examination Report, dated Jul. 7, 2009, in connection with corresponding European Application No. 07 709 034.8, 2 pages.
Response to Examination Report, filed Nov. 11, 2009, in connection with corresponding European Application No. 07 709 034.8, 12 pages.
Examination Report, dated Nov. 24, 2009, in connection with corresponding European Application No. 07 709 034.8.
Response to Examination Report, dated Apr. 1, 2010, in connection with corresponding European Application No. 07 709 034.8, 12 pages.
Examination Report, dated Dec. 7, 2010, in connection with corresponding European Application No. 07 709 034.8, 5 pages.
Response to Examination Report, dated Apr. 4, 2011, in connection with corresponding European Application No. 07 709 034.8, 10 pages.
Office Action, dated Mar. 14, 2012, in connection with corresponding Japanese Patent Application No. 2008-556244, 3 pages.
Restriction Requirement, dated Jun. 4, 2013, in connection with U.S. Appl. No. 13/669,414, 9 pages.
Response to Restriction Requirement, dated Jul. 3, 2013, in connection with U.S. Appl. No. 13/669,414, 6 pages.
Office Action, dated Aug. 8, 2013, in connection with U.S. Appl. No. 13/669,414, 23 pages.
Response to Office Action, dated Nov. 8, 2013, in connection with U.S. Appl. No. 13/669,414, 22 pages.
Examination Report, dated Dec. 12, 2013, in connection with European Patent Application No. 07 709 034.8, 5 pages.
Office Action, dated Dec. 18, 2013, in connection with U.S. Appl. No. 13/669,414, 15 pages.
Response to Examination Report, dated Apr. 14, 2014, in connection with corresponding European Application No. 07 709 034.8, 9 pages.
Applicant Initiated Interview Summary, dated Apr. 29, 2014, in connection with U.S. Appl. No. 13/669,414, 13 pages.
Amendment After Final, dated May 5, 2014, in connection with U.S. Appl. No. 13/669,414, 10 pages.
Advisory Action, dated May 12, 2014, in connection with U.S. Appl. No. 13/669,414, 3 pages.
Amendment and Request for Continued Examination, dated May 19, 2014, in connection with U.S. Appl. No. 13/669,414, 11 pages.
Restriction Requirement, dated Sep. 5, 2014, in connection with U.S. Appl. No. 13/757,703, 10 pages.
Response to Restriction Requirement, dated Dec. 4, 2014, in connection with U.S. Appl. No. 13/757,703, 6 pages.
Office Action, dated Feb. 4, 2015, in connection with U.S. Appl. No. 13/669,414, 15 pages.
Office Action, dated Feb. 4, 2015, in connection with U.S. Appl. No. 13/757,703, 12 pages.
Communication pursuant to Article 94(3) EPC, dated Apr. 22, 2015, in connection with European Patent Application No. 07 709 034.8, 4 pages.
Amendment and Response, dated Aug. 4, 2015, to Office Action, dated Feb. 4, 2015, in connection with U.S. Appl. No. 13/669,414, 30 pages.
Amendment and Response, dated Aug. 4, 2015, to Office Action, dated Feb. 4, 2015, in connection with U.S. Appl. No. 13/757,703, 40 pages.
Response to Communication pursuant to Article 94(3) EPC, dated Aug. 17, 2015, in connection with European Patent Application No. 07 709 034.8, 7 pages.
Communication pursuant to Article 94(3) EPC, dated Sep. 4, 2015, in connection with European Patent Application No. 07 709 034.8, 3 pages.
Final Office Action, dated Oct. 28, 2015, in connection with U.S. Appl. No. 13/669,414, 19 pages.
Final Office Action, dated Oct. 28, 2015, in connection with U.S. Appl. No. 13/757,703, 17 pages.
Response to Communication pursuant to Article 94(3) EPC, dated Dec. 3, 2015, in connection with European Patent Application No. 07 709 034.8, 8 pages.
Amendment After Final, dated Feb. 3, 2016, in connection with U.S. Appl. No. 13/669,414, 10 pages.
Applicant Initiated Interview Summary, dated Mar. 1, 2016, in connection with U.S. Appl. No. 13/669,414, 3 pages.
Communication pursuant to Article 94(3) EPC, dated Jul. 15, 2016, in connection with European Patent Application No. 07 709 034.8, 4 pages.
Letter/Written Disclosure of the Supplemental Information Disclosure Statment for the above-referenced application, filed herewith on Jul. 17, 2017, 2 pages.
Response, dated Dec. 22, 2016, to Communication pursuant to Article 94(3) EPC, dated Jul. 15, 2016, in connection with European Patent Application No. 07 709 034.8, 10 pages.
Communication pursuant to Article 94(3) EPC, dated Mar. 14, 2017, in connection with European Patent Application No. 07 709 034.8, 4 pages.
Response, dated Jul. 14, 2017, to Communication pursuant to Article 94(3) EPC, dated Mar. 14, 2017, in connection with European Patent Application No. 07 709 034.8, 17 pages.

PEPTIDE HAVING CELL MEMBRANE PENETRATING ACTIVITY

RELATED APPLICATIONS

This application is a divisional of U.S. application Ser. No. 13/669,414, filed Nov. 5, 2012, which is a continuation of U.S. application Ser. No. 12/280,077, filed Nov. 3, 2008, which is the U.S. National Stage application of PCT/KR2007/000885, filed Feb. 20, 2007, which claims priority to Korean Patent Application No. 10-2006-0016156, filed Feb. 20, 2006, to Kyunglim Lee, Moonhee Kim and Miyoung Kim. The subject matter of each of the above-mentioned applications is incorporated by reference in its entirety.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Apr. 22, 2016, is 23 kilobytes in size, and titled 380DUSseq001.txt.

TECHNICAL FIELD

The present invention relates to a peptide having cell membrane penetrating activity, a transmembrane carrier comprising the peptide having cell membrane penetrating activity as an effective component, a transmembrane complex consisting of the peptide having cell membrane penetrating activity combined with a target substance, a transfection kit comprising the peptide having cell membrane penetrating activity and the target substance, use of the peptide having cell membrane penetrating activity for the manufacture of a transmembrane complex, use of the transmembrane complex for the manufacture of a medicament, and a method for delivering a target substance into cell interior which comprises administrating to a subject with a transmembrane complex consisting of the peptide having cell membrane penetrating activity combined with a target substance to induce transduction of the transmembrane complex into cell interior.

BACKGROUND ART

Recently, various methods have been developed for delivering macromolecules such as therapeutic drug, peptides and proteins into cells in vitro and in vivo.

In vitro methods include electroporation, membrane fusion with liposomes, high velocity bombardment with DNA-coated microprojectiles, incubation with calcium-phosphate-DNA precipitate, DEAE-dextran mediated transfection, infection with modified viral nucleic acids, and direct micro-injection into single cells. But such methods are of extremely limited usefulness for delivery of proteins.

Delivery of macromolecules into cells in vivo has been accomplished with scrape loading, calcium phosphate precipitates and liposomes. However, these techniques have, up to date, shown limited usefulness for in vivo cellular delivery.

General methods for efficient delivery of biologically active proteins into intact cells, in vitro and in vivo include chemical addition of a lipopeptide (P. Hoffmann et al., 1988) or a basic polymer such as polylysine or polyarginine etc. (W-C. Chen et al., 1978)

Folic acid has been used as a transport moiety (C. P. Leamon and Low, 1991). However, these methods have not proved to be highly reliable or generally useful.

Recently to introduce macromolecules such as a protein into a cell interior, gene therapy becomes in the limelight but this have also problems in that targeting is incorrect. As a alternative, research on protein transduction or protein therapy is actively progressed.

Protein transduction domain (PTD) was first reported that purified human immunodeficiency virus type-1 ("HIV") TAT protein is taken up from the surrounding medium by adding it to human cells growing in culture medium (Green et al., 1988, Frankel et al., 1988). After this report, drosophila homeotic transcription factor, antennapedia (Antp) (Joliot et al., 1991) and herpes simplex virus-1 DNA-binding protein, VP22 (Elliot et al 1997) were also identified.

In comparison of amino acid sequences of the PTDs such as TAT, Antp and VP22 etc., basic amino acids such as arginine and lysine exist for the most part (TABLE 1) and this sequence potentiates easy approach near to the negatively charged phospholipid bilayer and penetration into the cell interior. Protein sequences having penetrating activity were named as protein transduction domains (PTDs).

TABLE 1

| PTD | Amino Acid Sequences | SEQ ID NO: |
| --- | --- | --- |
| HIV-1 TAT | Tyr-Gly-Arg-Lys-Lys-Arg-Arg-Gln-Arg-Arg-Arg | 82 |
| HSV VP22 | Asp-Ala-Ala-Thr-Ala-Thr-Arg-Gly-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu | 83 |
| Antp | Arg-Gln-Iso-Lys-Iso-Trp-Phe-Gln-Asn-Arg-Arg-Met-Lys-Trp-Lys-Lys | 84 |

In particular, recombinant expression vector was developed by using a peptide containing 11 amino acids of TAT 47-57 and TAT fusion proteins were prepared by linking the TAT peptide to other peptides or proteins and so introduction of full-length protein into intracellular compartment became possible without the limitation of size or function (Nagahara et al., 1988).

As PTDs can be linked with other peptide or proteins to form fusion protein and then be transduced into cell interior, there are many attempts to transduce therapeutic drug, peptide, protein etc. into cell interior using PTDs.

Recently, it has been known for PTDs which do not contain lots of basic amino acid residues. Also, it has been reported that PTDs penetrate phosphoelipid bilayer of cell membrane by helix conformation.

TCTP (translationally controlled tumor protein) is a protein known as IgE-dependent histamine-releasing factor (HRF) as reported by MacDonald et al. (1995). TCTP had been known as tumor-specific protein until 1980' and the synthesis thereof was assumed to be related to proliferative stage of tumor. TCTP was reported as a tumor protein of 21 kDa, p21 in mouse erythroleukemia cell line (Chitpatima et al., 1988). Also, it was revealed that p23, relating to cell growth in Ehrlich ascites tumor is the same as TCTP/HRF (Bohm et al, 1989).

TCTP is frequently found in tumor cell, particularly growing vigorously, and exists in cytoplasm. It is a known protein consisting of 172 amino acids (NCBI accession #P13693 (*Homo sapiens*)) and shows high homology between species. 45 amino acids at its C-terminal form basic domain. Because such domain has about 46% homology with MAP-1B, microtubule-associated protein, it was also assumed that HRF is a microtubule-associated protein. Gachet, et al. (1997) observed that HRF is distributed consistently along with the cytoskeletal network to some extent using confocal microscope, which suggests that HRF binds to the cytoskeleton.

TCTP expression is characterized by that mRNA is maintained in regular level, but in case that exterior stimulus such as serum exists, it is transformed to polysome to be translated. According to the characteristic, it was named as 'Translationally Controlled Tumor Protein (TCTP)' (Thomas et al., 1981; Thomas and Thomas., 1986). It was also reported that TCTP mRNA is suppressed during translation, but when it receives cell division signal, it is activated and translated to protein (Thomas and Thomas, 1986).

TCTP/HRF is considered as a histamine releasing material interacting with basophil or mast cell and related to allergic inflammatory response.

MacDonald, et al. (1995) also found that though HRF is an intracellular protein, HRF in the outside of cells stimulates IgE-sensitized basophils to release histamine (Schroeder, et al., 1996). Schroeder, et al. (1997) observed that HRF can augment the anti-IgE-induced histamine release from all basophils, regardless of the IgE absence, and thus suggested that HRF exerts its function by binding to cell membrane receptors, not by binding with IgE.

The present inventors have previously reported that TCTP/HRF is interacted with third cytoplasmic domain (CD3) of subunit of (Na,K)ATPase thereby suppressing the activity of (Na,K)ATPase (as shown in KR Patent Application No. 10-2001-0027896) (Jung et al., 2004).

At the same time the present inventors reports that TCTP/HRF can pass through cell membrane. Since the amino acid sequence of TCTP/HRF has no part consisting of plenty of basic amino acids, arginine or lysine, which is a characteristic of representative PTDs, and no similar amino acid sequences to those of other PTDs, the present inventors considered TCTP has a domain which is different to other known PTDs in aspect of the protein structures.

In whole structure of TCTP, N- and C-terminus get loose and exposed and middle part forms a spherical shape.

In prediction of third structure, there are three helixes, wherein first helix (H1) is very short, second (H2) and third helix (H3) are exposed to outside. By H2 and H3 structure of TCTP in *Schizosaccharomyces pombe*, basic amino acids are distributed to outside of helix (Thaw et al., 2001) and so H2 and H3 were predicted to be related to protein transduction activity. However, by a test result, this helix part had nothing to do with translocation.

Therefore if we identify amino acid sequences with protein transduction function in TCTP/HRF, it may be possible to find new types of PTD, as well as to make a new drug delivery system though a novel vector development using these.

The present inventors made a constant effort for looking for PTD in TCTP and, as a result, isolated protein transduction domain composed of very different amino acids in comparison with well-known PTDs. On the basis of this result, the present inventors have established the present invention by confirming that this domain shows remarkably high cell penetrating activity than well-known PTDs.

DISCLOSURE OF INVENTION

Technical Problem

It is an object of the present invention to provide a peptide having cell membrane penetrating activity, a transmembrane carrier comprising the peptide having cell membrane penetrating activity as an effective component, a transmembrane complex consisting of the peptide having cell membrane penetrating activity combined with a target substance, a transfection kit comprising the peptide having cell membrane penetrating activity and the target substance, use of the peptide having cell membrane penetrating activity for the manufacture of a transmembrane complex, use of the transmembrane complex for the manufacture of a medicament, and a method for delivering a target substance into cell interior which comprises administrating to a subject with a transmembrane complex consisting of the peptide having cell membrane penetrating activity combined with a target substance to induce transduction of the transmembrane complex into cell interior.

Technical Solution

This invention provides a peptide having cell membrane penetrating activity, composed of the following amino acid sequence:

R1-R2-R3-R4-R5-R6-R7-R8-R9-R10

In the above formula,

R1 may be deleted or one amino acid selected from M, A, Q, C, F, L or W,

R2 may be deleted or one amino acid selected from I or A,

R3 may be one amino acid selected from I or A,

R4 may be one amino acid selected from Y, A, F, S or R,

R5 may be one amino acid selected from R, A or K,

R6 may be one amino acid selected from D, A, I or R,

R7 may be deleted or one amino acid selected from L, K, A, E or R,

R8 may be deleted or one amino acid selected from I, K or A,

R9 may be deleted or one amino acid selected from A, S, E, Y or T,

R10 may be deleted or one amino acid selected from A, H, K or E, and if R10 is K or H, the amino acid(s) selected from K, KK, R, RR or HH may be added thereto.

In one embodiment of the present invention, the amino acid sequence may be SEQ ID No.: 1.

In one embodiment of the present invention, the amino acid sequence may be SEQ ID Nos.: 2-7.

Also, in one embodiment of the present invention, the amino acid sequence may be an amino acid sequence which one amino acid of SEQ ID No.: 2 is substituted with alanine. The above amino acid sequence may be, for example, an amino acid sequence selected from SEQ ID Nos.: 8-16, particularly SEQ ID No.: 13.

In addition, in an embodiment of the present invention, the amino acid sequence may be an amino acid sequence selected from SEQ ID Nos.: 20-54. The above sequence may be, for example, an amino acid sequence selected from SEQ ID Nos.: 22, 26, 27 or SEQ ID Nos.: 31-54.

In the present invention, 'cell membrane penetrating protein domain' means protein sequence having penetrating activity into cell interior (cytoplasm, nucleus) across plasma membrane.

A peptide having cell membrane penetrating activity of the present invention is a novel cell membrane penetrating protein domain that has no similarity in sequences with well-known TAT, VP22 and Antp PTDs (Protein Transduction Domains).

The present invention provides a peptide having cell membrane penetrating activity consisting of the amino acid sequence of SEQ ID No.: 1. The present invention also provides a peptide having cell membrane penetrating activity consisting of one amino acid sequence selected from SEQ ID Nos.: 2-7.

According to one example of the present invention, the peptide having cell membrane penetrating activity consisting of the amino acid sequence of SEQ ID No.: 1, 2, 3 or 4 shows excellent cell penetrating activity in comparison with conventional TAT, and intracellular penetrating efficiency shows a rapidly increasing mode when treatment concentration becomes high and incubation time becomes long.

In detail, when cell penetrating activity was measured by using the residues of TCTP from $1^{st}$ to $10^{th}$[TCTP(1-10), SEQ ID No.: 1], cell penetrating activity of TCTP(1-10) show over 3 times activity when treated for 15 minutes in 50 µM and 6 times activity when treated for 15 minutes in 100 µM, compared to that of TAT. In case of treatment for 2 hours, cell penetrating activity at concentration of 50 µM and 100 µM of TCTP(1-10) were higher than those of TAT about 29 times and 30 times, respectively.

Also, compared with the case of treatment for 15 minutes, cell penetrating activity showed an increased fashion in the incubation time of 2 hours.

In addition, a peptide comprising amino acid residues of TCTP(1-9)(SEQ ID No.: 2), TCTP(1-8)(SEQ ID No.: 3) or TCTP(2-10)(SEQ ID No.: 4) showed more excellent penetrating activity than well-known TAT(47-58) peptide. Of these, cell penetrating activity was excellent in the order of TCTP(1-10)(SEQ ID No.: 1), TCTP(1-9)(SEQ ID No.: 2), TCTP(1-8)(SEQ ID No.: 3) and TCTP(2-10)(SEQ ID No.: 4), and when 1st amino acid of TCTP was existing, cell penetrating activity was more excellent.

Length of the peptides, as a common length of cell membrane penetrating protein domain accepted in this art, may vary within the scope of, preferably, 9-15 residues, and more preferably, 9-10 residues.

A peptide having cell membrane penetrating activity of the present invention may be prepared by artificial synthesis or by isolating the sequence of TCTP(1-10)(SEQ ID No.: 1), TCTP(1-9)(SEQ ID No.: 2), TCTP(1-8)(SEQ ID No.: 3) or TCTP(2-10)(SEQ ID No.: 4) from TCTP.

Synthesis of the peptide of the present invention may be performed, for example, by using an instrument or by using genetic engineering.

In case of synthesis by using an instrument, synthesis can be performed by using Fmoc solid-phase method on automatic peptide synthesizer (PeptrEX-R48, Peptron). After purifying the synthesized peptide from resin, the peptide can be purified and analyzed by reverse-phase HPLC (Prominence LC-20AB, Shimadzu, Japan) with Shiseido capcell pak C18 analytic RP column. After synthesis is completed, the peptide can be identified by a mass spectrometer (HP 1100 Series LC/MSD, Hewlett-Packard, Roseville, USA).

In case of isolation by genetic engineering, nucleic acid sequences corresponding to a desired peptide can be introduced into recombinant vector for protein expression, then the expression of peptide coding region can be induced by IPTG in E. coli bacteria like a BL21(λDE3) or BL21(λDE3) pLys, that is deficient in proteases, and the peptide can be purified.

The present invention also provides a peptide having cell membrane penetrating activity, composed of the amino acid sequence of SEQ ID Nos.: 8-16.

According to an example of the present invention, among the amino acid sequences that one amino acid of SEQ ID No.: 2 is substituted with alanine, alanine-substituent of 6th residue, aspartic acid(SEQ ID No.: 13), showed 2.5 times increased penetrating activity than WT(wild type) peptide at a low concentration of 10 µM and alanine-substituents of 5th and 7-9th residue(R, L, I, S)(SEQ ID Nos.: 12, 14-16) showed a little decreased but still showed activity. Activity of alanine-substituents of 1st-4th residues(M, I, I, Y)(SEQ ID Nos.: 8-11) was suddenly decreased but maintained functionally like a WT peptide. Therefore, a peptide having cell membrane penetrating activity of the present invention comprises the peptide consisting of one amino acid sequence selected from SEQ ID Nos.: 8-16.

The present invention also provides a peptides having cell membrane penetrating activity, consisting of one amino acid sequence selected from SEQ ID No.: 22, 26, 27, or 31-54.

In an example of the present invention, the peptides of SEQ ID Nos.: 20-30 were prepared by deletion, substitution or addition of one or more amino acids in SEQ ID No.: 1. As a result, the peptides consisting of SEQ ID No.: 22, 26 or 27 showed better penetrating activity than TAT(100 µM). On the basis of these penetration data, the peptides of SEQ ID Nos.: 31-45 were synthesized repeatedly and these peptides showed better penetrating activity than TAT in 10 µM. On the basis of above data, the peptides of SEQ ID Nos.: 46-54 were prepared as various mutant forms of SEQ ID No.: 1, then measured for cell penetrating activity. As a result, the peptide of SEQ ID No.: 49 had excellent activity compared with TAT and the peptides of SEQ ID Nos.: 46-54 showed a similar or better activity compared with TAT and excellent activity compared with TCTP(1-10)(SEQ ID No.: 1). Therefore, a peptide having cell membrane penetrating activity of the present invention comprises the peptides consisting of SEQ ID Nos.: 22, 26, 27 and 31-54.

Length of the peptides, as a common length of cell membrane penetrating protein domain accepted in this art, may vary within the scope of, preferably 5-15 residues, and more preferably 8-10 residues.

The peptide of the present invention may be prepared by artificial synthesis or by isolating the sequence of TCTP(1-10)(SEQ ID No.: 1), TCTP(1-9)(SEQ ID No.: 2), TCTP(1-8)(SEQ ID No.: 3) or TCTP(2-10)(SEQ ID No.: 4) and modifying these sequences.

Synthesis of the peptides may be prepared by same synthesis methods as described above.

The present invention also provides a transmembrane carrier comprising the peptide having cell membrane penetrating activity as an effective component. The peptide having cell membrane penetrating activity provides a use as a transmembrane carrier for penetrating target substance across plasma membrane.

In addition, the present invention provides a transmembrane complex consisting of the peptide having cell membrane penetrating activity combined with a target substance.

The term 'target substance' of the present invention means a molecule that may, having penetrated into a cell (either the cytoplasm or the nucleus), become involved in the regulation of physiological activity, have a pharmacological effect, or otherwise maintain biological activity in the intracellular compartment.

Target substance of the present invention, for example, may comprise nucleic acid including DNA and RNA, chemical compound such as drug, carbohydrate, lipid or glycolipid etc. as non-protein range molecule, and enzyme, regulation factor, growth factor, antibody, cytoskeletal factor etc. as protein range molecule.

A peptide having cell membrane penetrating activity of the present invention may be linked to one or more target substances by physically/chemically covalent bond or non-covalent bond, or by mediators in incorporated or fused forms.

In detail, if the target substance is a non-protein range molecule, a peptide having cell membrane penetrating activity of the present invention may be linked to the target substance by covalent bond, then the complex may be exposed to target cell group. In another example, the target substances may be non-covalently linked to a peptide having cell membrane penetrating activity of the present invention. For instance, if the target substance is a nucleic acid, it may be incorporated with a peptide having cell membrane penetrating activity of the present invention, in forms of lipid based vehicle, then exposed to target cell group.

In case that the target substance is a protein, fusion protein incorporated with a peptide having cell membrane penetrating activity of the present invention can be prepared by obtaining cDNA of the protein(the target substance) through PCR and cloning cDNA using vectors. If it is impossible, the protein may be fused chemically. For example, fusion protein can be prepared by connecting the target substance to linker, then reacting with the peptide having cell membrane penetrating activity to form linkage.

In particular, when the target substance is a protein, the complex may be penetrated in forms of fusion protein. In this case, cell penetrating complex of the present invention may be prepared as follows.

First, recombinant expression vector is prepared to generate a fusion gene encoding a peptide having cell membrane penetrating activity-target substances conjugate.

Nucleic acids encoding above fusion protein include the nucleic acid sequence encoding a peptide having cell membrane penetrating activity and the nucleic acid sequence encoding a protein as target substance. For example, these nucleic acid sequences may comprise sequences consisting of SEQ ID Nos.: 17-18 or 55-81.

Nucleic acid sequences of SEQ ID Nos.: 17-18 or 55-81 are as follows.

| Classification | Nucleic Acid Sequences (Homo sapiens) | SEQ ID No. |
| --- | --- | --- |
| Nucleic acid for SEQ ID No.: 1(TCTP1-10) | atgattatctaccgggacctcatcagccac | 17 |
| Nucleic acid for SEQ ID No.: 2(TCTP1-9) | atgattatctaccgggacctcatcagc | 18 |
| Nucleic acid for SEQ ID No.: 22(TCTP-CPP#3) | atgattattttcgcgatctgattagccat | 55 |
| Nucleic acid for SEQ ID No.: 26(TCTP-CPP#7) | atgattatttatcgcgcgctgattagccataaaaaa | 56 |
| Nucleic acid for SEQ ID No.: 27(TCTP-CPP#8) | atgattatttatcgcattgcggcgagccataaaaaa | 57 |
| Nucleic acid for SEQ ID No.: 31(TCTP-CPP#12) | atgattattttcgcattgcggcgagccataaaaaa | 58 |
| Nucleic acid for SEQ ID No.: 32(TCTP-CPP#13) | atgattattttcgcgcgctgattagccataaaaaa | 59 |
| Nucleic acid for SEQ ID No.: 33(TCTP-CPP#14) | atgattattttcgcgcggcggcgagccataaaaaa | 60 |
| Nucleic acid for SEQ ID No.: 34(TCTP-CPP#15) | tttattattttcgcattgcggcgagccataaaaaa | 61 |
| Nucleic acid for SEQ ID No.: 35(TCTP-CPP#16) | ctgattattttcgcattgcggcgagccataaaaaa | 62 |
| Nucleic acid for SEQ ID No.: 36(TCTP-CPP#17) | tggattattttcgcattgcggcgagccataaaaaa | 63 |
| Nucleic acid for SEQ ID No.: 37(TCTP-CPP#18) | tggattattttcgcgcggcggcgagccataaaaaa | 64 |
| Nucleic acid for SEQ ID No.: 38(TCTP-CPP#19) | tggattattttcgcgcgctgattagccataaaaaa | 65 |
| Nucleic acid for SEQ ID No.: 39(TCTP-CPP#20) | agattatuttcgcattgggcgtatcataaaaaa | 66 |
| Nucleic acid for SEQ ID No.: 40(TCTP-CPP#21) | tggattattttcgcattgcggcgtatcataaaaaa | 67 |
| Nucleic acid for SEQ ID No.: 41(TCTP-CPP#22) | atgattattttcgcattgcggcgacccataaaaaa | 68 |
| Nucleic acid for SEQ ID No.: 42(TCTP-CPP#23) | tggattattttcgcattgcggcgacccataaaaaa | 69 |
| Nucleic acid for SEQ ID No.: 43(TCTP-CPP#24) | atgattattttaaaattgggcgagccataaaaaa | 70 |
| Nucleic acid for SEQ ID No.: 44(TCTP-CPP#25) | tggattattttaaaattgcggcgagccataaaaaa | 71 |
| Nucleic acid for SEQ ID No.: 45(TCTP-CPP#26) | atgattattttgcgattgcggcgagccataaaaaa | 72 |
| Nucleic acid for SEQ ID No.: 46(TCTP-CPP#27) | ctgattattttcgcattctgattagccataaaaaa | 73 |

-continued

| Classification | Nucleic Acid Sequences (Homo sapiens) | SEQ ID No. |
|---|---|---|
| Nucleic acid for SEQ ID No.: 47(TCTP-CPP#28) | atgattattttcgcattctgattagccataaaaaa | 74 |
| Nucleic acid for SEQ ID No.: 48(TCTP-CPP#29) | ctgattattttcgcattctgattagccatcgccgc | 75 |
| Nucleic acid for SEQ ID No.: 49(TCTP-CPP#30) | ctgattattttcgcattctgattagccatcatcat | 76 |
| Nucleic acid for SEQ ID No.: 50(TCTP-CPP#31) | ctgattattttcgcattctgattagccataaa | 77 |
| Nucleic acid for SEQ ID No.: 51(TCTP-CPP#32) | ctgattatattcgcattetgattagccatcgc | 78 |
| Nucleic acid for SEQ ID No.: 52(TCTP-CPP#33) | ctgattattttcgcattctgattagccat | 79 |
| Nucleic acid for SEQ ID No.: 53(TCTP-CPP#34) | ctgattattttgcgattgcggcgagccataaaaaa | 80 |
| Nucleic acid for SEQ ID No.: 54(TCTP-CPP#35) | ctgattattttgcgattctgattagccataaaaaa | 81 |

Since codons encoding one amino acid are several, nucleic acid sequences encoding the peptide of the present invention include all nucleic acid sequence encoding the peptide of the present invention besides nucleic acid sequences listed in above table.

Recombinant expression vector of the present invention may include conventional promoter for expression, termination factor, selection marker, reporter gene, tag sequence, restriction enzyme recognitions site, multi-cloning site and so on.

Transfection methods to host using recombinant expression vector of the present invention may be a heat shock or electroporation etc. which is known in the art.

After fusion proteins are expressed under proper conditions in transfected host cell as above, fusion proteins, which consist of a peptide having cell membrane penetrating activity and a protein as target substance, may be purified by conventional methods known in the art.

In addition, the present invention provides a transfection kit comprising the peptide having cell membrane penetrating activity and the target substance. Transfection kits are optimized systems to introduce easily DNA/RNA to intracellular compartment of mammalian cell. There are up to now calcium-phosphate method, methods using lipid complex or dextran complex, but limitations are that efficiency of these methods is $1/10^6$-$1/10^2$ and depend on cell type. To overcome these limitations, transfection kits using the peptide having cell membrane penetrating activity, may be utilized.

The transfection kit of the present invention may further comprise a binding factor combining the peptide with the target substance. The binding factor means specific DNA/RNA sequences including transcriptional factor, virus protein, or whole body or a part of protein that are capable to bind to target substance. For example, Gal4 is a DNA binding factor. Gal4 is a transcriptional factor widely used in eukaryote, prokaryote and virus. DNA/RNA binding factors may be used by vector expressing PTDs and fusion proteins in vivo and vitro. Also, incorporation between DNA/RNA binding factors and PTDs may be accomplished by chemical interaction, physical interaction or noncovalent interaction.

If fusion complexes between a peptide having cell membrane penetrating activity of the present invention and DNA/RNA are treated outside the cells, it can be overcome both efficiency and limitation depending on the cell type. Using both a peptide having cell membrane penetrating activity of the present invention and DNA/RNA binding factors, it is capable that DNA/RNA is introduced into cytoplasm and nucleus of various cells in vivo and in vitro. Particularly, introduction method can be accomplished by various route including intramuscular, intraperitoneal, intravenous, oral, subcutaneous, intracutaneous, intranasal introduction and inhalation.

In addition, target substance may include one or more biological regulation substances selected from a group consisting of protein, lipid, carbohydrate or chemical and transfection kits of the present invention can introduce above target substance into cytoplasm and nucleus of various cells in vivo and in vitro. Fusion between PTD and target substance can be accomplished by chemical, physical covalent interacation or noncovalent interaction.

Transfection kit of the present invention provides new technology about gene therapy and DNA/RNA vaccine according to the methods of the present invention and can express transiently or permanently and be used in clinical applications such as gene therapy and DNA/RNA vaccine as well as basic research.

Also, the present invention provides a use of the peptide having cell membrane penetrating activity for the manufacture of a transmembrane complex and a method for preparing transmembrane complexes by combining target substance with the peptide having cell membrane penetrating activity.

In addition, the present invention provides a use of the transmembrane complex consisting of the peptide having cell membrane penetrating activity combined with a target substance for the manufacture of a medicament and a method for manufacturing a medicament which comprises mixing the transmembrane complex consisting of the peptide having cell membrane penetrating activity combined with a target substance, with a pharmaceutically acceptable carrier. The pharmaceutically acceptable carrier is well known to a skilled artisan, and the skilled artisan can select and use the pharmaceutically acceptable carrier which is proper for introduction to a living body.

Further, the present invention provides a method for delivering a target substance into cell interior which comprises administrating to a subject with a transmembrane complex consisting of the peptide having cell membrane penetrating activity combined with a target substance to induce transduction of the transmembrane complex into cell interior.

If the target substance is non-protein range molecule, it may be covalently attached to the peptide having cell membrane penetrating activity of the present invention, and the complex may be exposed to target cell group. In another example, the target substance may be non-covalently attached to the peptide having cell membrane penetrating activity of the present invention, for example, if the target substance is a nucleic acid, the complex may be exposed to target cell group in forms of lipid based vehicle incorporated with the peptide having cell membrane penetrating activity of the present invention.

The 'subject' may be mammal including human. The transmembrane complex can be administrated by various route including intramuscular, intraperitoneal, intravenous, oral, subcutaneous, intracutaneous, mucosal administration and inhalation.

Dose of the transmembrane complex consisting of the peptide having cell membrane penetrating activity combined with a target substance, is variable according to a therapeutically effective amount of the target substance and penetrating activity of the peptide, and so it is not limited to a specific dose. Only, for example, if the target substance is a nucleic acid, the dose of target substance may be 10~1000 µg/kg and the dose of the peptide of the present invention may be 0.1 mg-10 mg/kg.

In addition, the present invention provides a method for treating related diseases by administrating to a subject with the transmembrane complex consisting of the peptide having cell membrane penetrating activity combined with a target substance thereby introducing the target substance into a cell.

The kind of the disease desired to treatment may be varied depending on the target substance intended to administrate into cell interior.

The 'subject' may be mammal including human. The transmembrane complex can be administrated by various route including intramuscular, intraperitoneal, intravenous, oral, subcutaneous, intracutaneous, mucosal administration and inhalation.

Also, the present invention provides a nucleic acid sequence encoding the peptide having cell membrane penetrating activity. For example, the present invention provides a nucleic acid encoding the peptide having cell membrane penetrating activity, consisting of an amino acid sequences selected from SEQ ID No.: 1, 2, 22, 26, 27 or 31-54.

The nucleic acid may be DNA or RNA of single chain or double chain and be prepared by synthesizing artificially or isolating from organism-derived TCTP genes. For example, the nucleic acids encoding the peptides consisting of SEQ ID Nos.: 1, 2, 22, 26, 27 or 31-54, represent the nucleic acid sequences of SEQ ID Nos.: 17-18, or 55-81, respectively.

Since codons encoding one amino acid are several, nucleic acid sequences encoding the peptide of the present invention include all nucleic acid sequences encoding the peptide of the present invention, and are not limited to the nucleic acid sequences listed in above table. For example, sequence encoding alanine in amino acid sequence may be gca, gcc, gcg or gct.

The peptide of the present invention having cell membrane penetrating activity has a prominent effect in delivery as compared with TAT-derived peptide. Thus, the peptide having cell membrane penetrating activity of the present invention, the transmembrane complex consisting of the peptide combined with a target substance, and the method for delivering a target substance into a cell using the transmembrane complex has applications on intracellular delivery in various research fields as well as on therapeutics of specific diseases where targeting of drugs is required at high efficiency. Accordingly, the peptide having cell membrane penetrating activity of the present invention, the transmembrane complex consisting of the peptide combined with a target substance, and the method for delivering a target substance into a cell using the transmembrane complex is very useful as drug delivery systems.

In order that the invention described herein may be more fully understood, the following examples are set forth. It should be understood that these examples are for illustrative purposes only and are not to be construed as limiting this invention in any manner.

Advantageous Effects

The peptide having cell membrane penetrating activity of the present invention has a prominent penetrating efficiency as compared with the activities of prior TAT-derived peptides and so the peptide has applications on intracellular delivery in various research fields as well as on therapeutics of specific diseases where targeting of drugs is required high efficiently. Accordingly, the peptide having cell membrane penetrating activity of the present invention, the transmembrane complex consisting of the peptide combined with a target substance, and the method for delivering a target substance into a cell using the transmembrane complex is very useful as drug delivery systems.

MODE FOR INVENTION

[Example 1] Mapping of PTD Using Various Deletion Forms of TCTP

In order to confirm the region of the TCTP acting as PTD, various deletion constructs were prepared and then used in the experiment as follows.

1) Isolation and Purification of Deletion Forms of TCTP

Figure 1A:
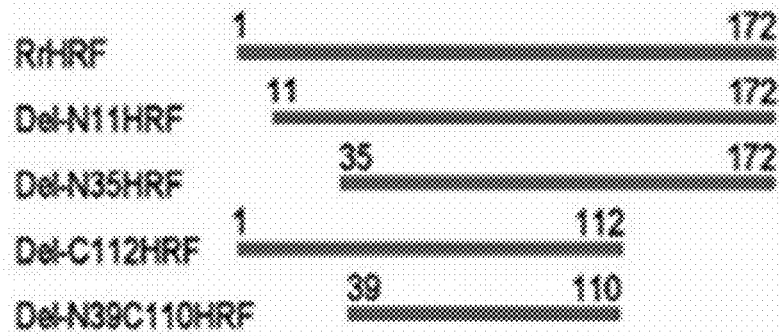
FIG. 1A and FIG. 1C are schematic diagrams showing various deletion forms of TCTP of the present invention.

To overexpress each of those deletion forms of TCTP (FIGS. 1a and 1c), pRSET vector that is capable of tagging 6 histidine was employed. Subcloning with DNA sequences corresponding to each deletion forms of TCTP was performed in the multicloning site of the vector. Then, the recombinant expression vector was introduced into *E. coli* BL21(DE3)(Novagen) or BL21(DE3)pLysS (Novagen). The expression of the deletion forms of TCTP was induced by IPTG (isopropyl (-D-thiogalactoside) for 3 hours, then the protein was isolated and purified by using Ni column which binds to polyhistidine.

2) Cell Culture and Treatment with the Protein

Figure 1B:
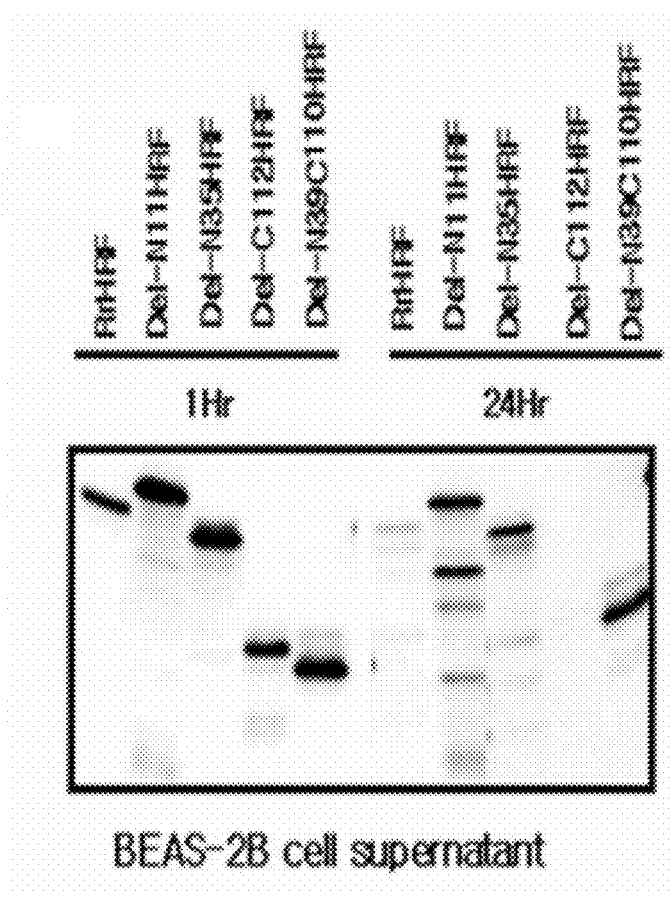
FIG. 1B and FIG. 1D are the western blot analysis results for cellular uptake of the various deletion forms of TCTP of FIG. 1A and FIG. 1C in BEAS-2B cell line.
Figure 1C:
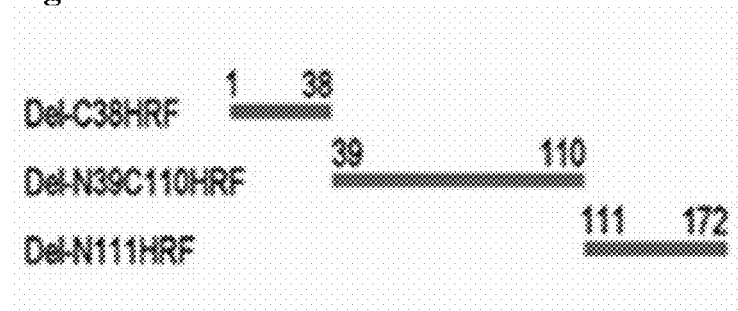

BEAS-2B cell was treated with the deletion form of TCTP at the concentration of 15 ug/ml BEAS-2B cell was treated with the deletion form of TCTP at the concentration of 15 ug/ml with anti-TCTP antibodies (FIG. 1b).

As shown in FIG. 1 b, full length TCTP existed in cell supernatants after incubation for 1 hour (Lane 1) but this protein disappeared 24 hours later (Lane 6). Also, in cell supernatant containing Del-C112HRF lacking C-terminus, the protein disappeared 24 later (Lane 9). On the other hands, remaining deletion forms of TCTP lacking N-terminus, Del-N11, N35 and N39C110HRF were still existing in cell supernatant 24 hours later (Lane 7, 8, 10).

Therefore, it could be known that PDT of TCTP exists in N-terminus. Particularly, since Del-NI 1HRF was still existed in cell supernatant 24 hours later (Lane 7), it seems that TCTP 1-10 plays a role as PDT.

In addition, it was examined whether TCTP proteins of the present invention could be transferred to cellular interior for a short time, 5 minutes or 30 minutes. The experiment was performed by same method as the above (FIG. 1d).

Figure 1D:
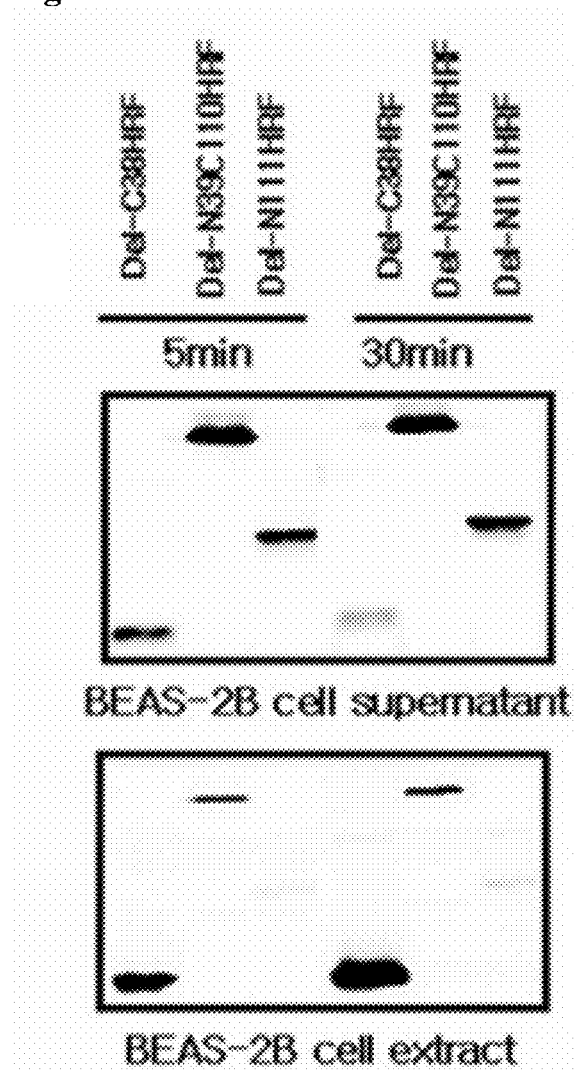

As shown in FIG. 1d, Del-C38HRF holding N-terminus of HRF disappeared after 30 minutes (Lane 4) in the supernatant while these proteins were found after 5 minutes (Lane1) and 30 minutes (Lane 4) in cell lysates.

Thus, N-terminus containing TCTP proteins of present invention can be transferred into cell interior for a short time, only several minutes to several tens minutes.

[Example 2] Confirmation of Cell Penetrating Efficiency of the Peptide of the Present Invention As shown in Example 1, in order to confirm that the N-terminus of TCTP can function as a PTD, the peptides consisting of N-terminus of TCTP were constructed and examined for cell penetrating efficiency.

1) Synthesis of Various Peptides Corresponding N-Terminus Amino Acid of TCTP

TCTP-derived peptides and control peptide, TAT 48-57 were synthesized as follow.

| Classification | Sequence of amino acid | SEQ ID No. |
|---|---|---|
| Residues of TCTP(1-10) | MIIYRDLISH | 1 |
| Residues of TCTP(1-9) | MIIYRDLIS | 2 |
| Residues of TCTP(1-8) | MIIYRDLI | 3 |
| Residues of TCTP(2-10) | IIYRDLISH | 4 |
| Residues of TCTP(1-7) | MIIYRDL | 5 |
| Residues of TCTP(1-6) | MIIYRD | 6 |
| Residues of TCTP(3-10) | IYRDLISH | 7 |
| Control TAT(48-57) | GRKKRRQRRR | 19 |

N-terminus of each peptides was labeled with fluorescence dye, rhodamine and C-terminus was protected. Peptide purity (>95%) was determined by HPLC. Synthesis of the peptides was requested to PEPTRON, Inc.

Negative control was a fluorescence dye, rhodamine (Molecular Probe) used to label in all peptides.

2) Cell Culture and Incubation of Peptides

HeLa cell line (ATCC) was propagated in DMEM (GIBCO) supplemented with 10% FBS (GIBCO) and 100 units/mL penicillin-streptomycin. Cells were grown in a 5% $CO_2$ incubator at 37° C.

HeLa cells were cultured in 48-well plate until they were 70~80% grown up before a day of the experiment. The cells were washed with DMEM of 37° C. twice, and TCTP-derived peptides synthesized in Example 2-1) were treated to the culture medium in a dose dependent manner (0, 1, 5, 10, 50, 100 μM), then the cells was incubated for 15 minutes or 2 hours in an $CO_2$ incubator at 37° C.

After the incubation, the cells were washed in cool PBS three times and immediately measured by a microplate fluorescence reader (BIO-TEK instruments, Inc., Vermont, USA) at emission 530 nm and excitation 590 nm for a measurement of rhodamine of intracellular uptake marker. The sensitivity of reader was set at 100 as a basic mode, but was lowered to 75 if the fluorescent signals were too strong. All experiments were conducted in triplet repeats for reproducibility (FIG. 2 and FIG. 3).

Figure 2:
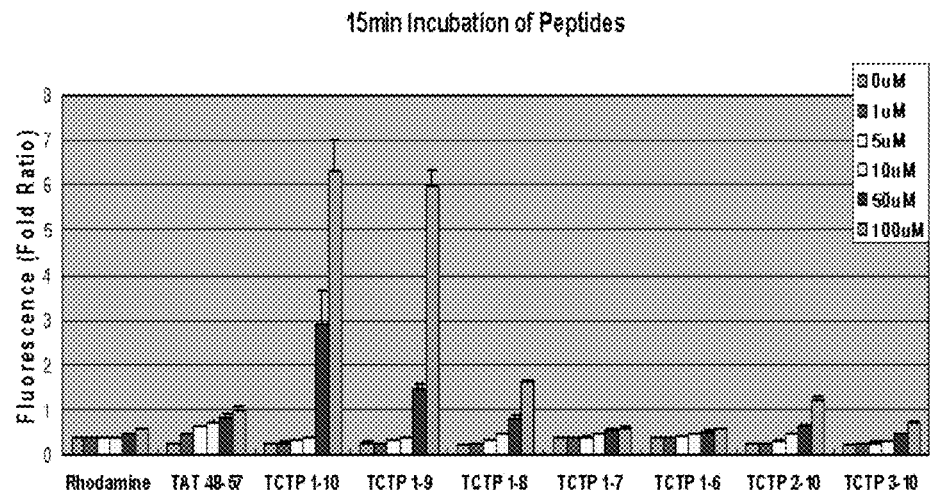
FIG. 2 shows a dose dependent cellular uptake after 15 minutes of treatment of TCTP-derived peptides.
Figure 3:
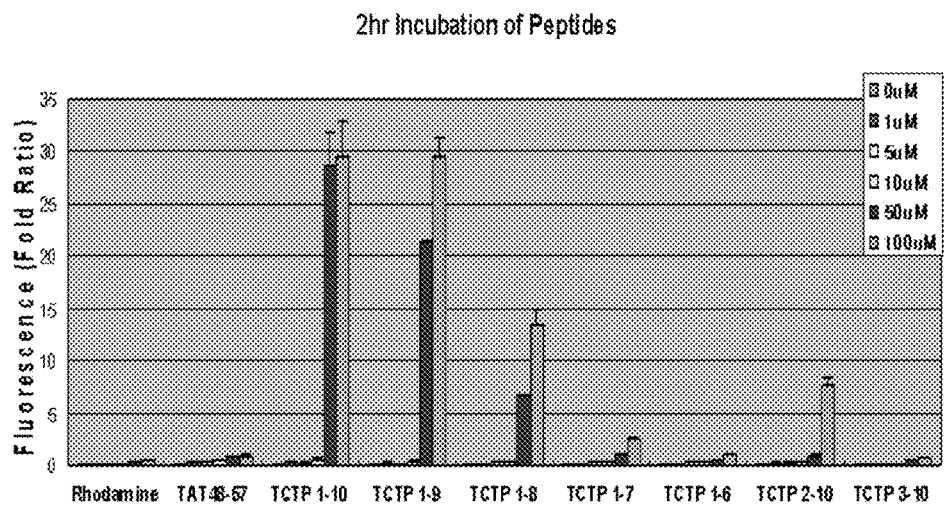
FIG. 3 shows cellular uptake after 2 hours of treatment of TCTP-derived peptides at various concentrations in Hela cell line.

As shown in FIG. 2 and FIG. 3, TAT, control peptide was transduced into cell in a dose and time-dependent manner as previously known.

TCTP (1-10), (1-9), (1-8) peptides of the present invention were translocated not in 1-10 μM but in 50-100 μM at 15 minutes (FIG. 2) or 2 hours (FIG. 3). In 50-100 μM, intracellular translocation was observed to be very high and could not detect due to a strong fluorescence particularly after 2 hours treatment and thus the sensitivity of reader was lowered to 75.

In FIG. 3, judging from the fact that there was no difference on translocation efficiency between 2 hour treatment at concentration 50 μM and that at 100 μM of TCTP (1-10) peptide, it seemed that TCTP(1-10) peptide was saturated at 50 μM. On the other side, TAT (48-57) peptide was saturated at 1 μM or more.

TCTP (2-10) peptide was not translocated at a concentration of 1 μM to 10 μM, but was more efficiently translocated at 100 μM after 15 minutes treatment of this peptide. After 2 hours, this peptide has similar cell membrane penetrating activity to control peptide, TAT(48-57), and was more efficiently translocated at 100 μM than control peptide.

So, it could be confirmed that TCTP (1-10), (1-9), (1-8) and (2-10) peptides having cell membrane penetrating activity of the prevent invention had superior ability than well-known PTD, TAT in their translocation efficiency.

For TCTP-derived peptide, it had been shown a sudden increase in translocation ability at the high concentration and these results might be caused by a difference in translocation mechanisms.

Consequently, it could be confirmed that TCTP (1-10), (1-9), (1-8) and (2-10) peptides having cell membrane penetrating activity of the present invention had superior ability than well-known PTD, TAT in their translocation efficiency. From among these peptides, translocation efficiency was superior in the order of TCTP (1-10), (1-9), (1-8) and (2-10) peptides, and existence of methionine ($1^{st}$ amino acid residue) of TCTP N-terminus was important.

[Example 3] Identification of Intracellular Translocation of TCTP-Derived Peptide by Fluorescence Microscope The intracellular translocation of the peptide was identified by fluorescence microscope.

HeLa cells were treated with TCTP (1-9)(SEQ ID No.: 2) at a concentration of 10 μM and 100 μM by the same method of Example 2-2). A point of difference was that HeLa cells were seeded in 12 well-plate covered a glass since the plastic plate had a property of fluorescence interference. After washing, cells on cover glass attached slide glass were observed (FIG. 4).

Figure 4:
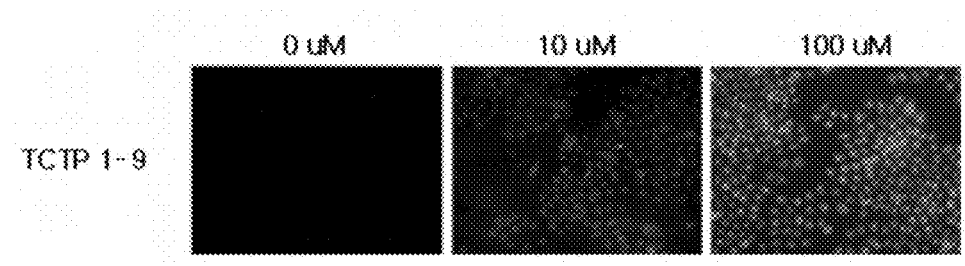
FIG. 4 shows fluorescence microscope images representing cellular uptake after 2 hours of treatment of the TCTP-derived peptides at various concentrations in HeLA cell line.

As shown in FIG. 4, the peptide of the present invention was weakly translocated at a low concentration of 10 μM and strongly at a high concentration of 100 μM. It was found that the peptides were distributed widely in cytoplasm and nucleus of the cell.

[Example 4] Identification of Intracellular Translocation of Peptide Substituents In order to confirm that substituent forms of the present peptide can function as a PTD, substituents of the peptide were constructed and examined for cell penetrating efficiency.

1) Construction of Peptide Substituents

Serial substituents of TCTP(1-9)(SEQ ID No.: 2) with alanine were synthesized as follows.

| Classification | Sequence of amino acid | SEQ ID No. |
|---|---|---|
| TCTP(1-9)M1A | AIIYRDLIS | 8 |
| TCTP(1-9)I2A | MAIYRDLIS | 9 |
| TCTP(1-9)I3A | MIAYRDLIS | 10 |
| TCTP(1-9)Y4A | MIIARDLIS | 11 |
| TCTP(1-9)R5A | MIIYADLIS | 12 |
| TCTP(1-9)D6A | MIIYRALIS | 13 |
| TCTP(1-9)L7A | MIIYRDAIS | 14 |
| TCTP(1-9)I8A | MIIYRDLAS | 15 |
| TCTP(1-9)S9A | MIIYRDLIA | 16 |

N-terminus of each peptide was labeled with fluorescence dye, rhodamine and C-terminus was protected. Peptide purity (>95%) was determined by HPLC. Synthesis of peptides of present invention was requested to PEPTRON, Inc.

2) Cell Culture and Incubation of Peptides

HeLa cell line was propagated in DMEM supplemented with 10% FBS and 100 units/mL penicillin-streptomycin. Cells were grown in a 5% $CO_2$ incubator at 37° C.

HeLa cells were cultured in 48-well plate until they were 70~80% grown up before a day of the experiment. The cells were washed with DMEM of 37° C. twice, and TCTP-derived peptides synthesized in Example 4-1) were treated to the culture medium in a dose dependent manner (0, 1, 10, 100 μM), then the cells was incubated for 15 minutes or 2 hours in an $CO_2$ incubator at 37° C.

After the incubation, the cells were washed in cool PBS three times and immediately measured by a microplate fluorescence reader at emission 530 nm and excitation 590 nm for a measurement of rhodamine of intracellular uptake marker. The sensitivity of reader was set at 100 as a basic, but was lowered to 75 if fluorescent signals were strong. All experiments were conducted in triplet repeats for reproducibility (FIG. 5 and FIG. 6).

Figure 5:
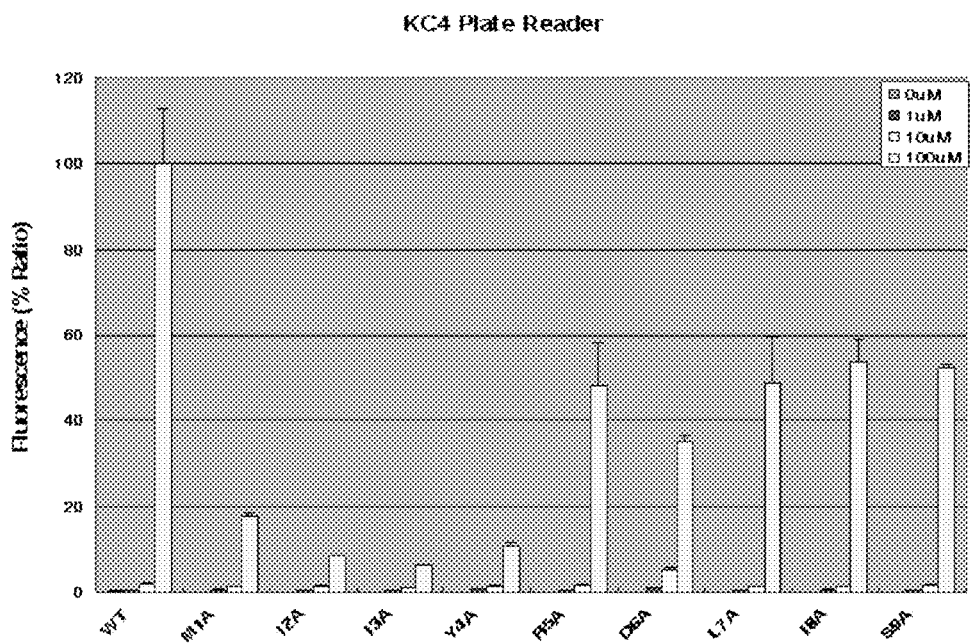
FIG. 5 shows cellular uptakes after 2 hours of treatment of substituents of TCTP-derived peptide at various concentrations at a sensitivity of 75.

As shown in FIG. 5, when fluorescence intensity of TCTP (1-9) at 100 μM was set to be 100%, the alanine substituents showing the largest decline in uptake were alanine substituents for amino acid residue 1,2,3,4(each M, I, I, Y) of TCTP(1-9)(each SEQ ID Nos.: 8,9,10,11), down by 80-90 percent.

On the other hand, alanine substituents for amino acid residue 5, 6, 7, 8, 9 (each R, D, L, I, S) of TCTP(1-9)(each SEQ ID Nos.: 12, 13, 14, 15, 16) were declined in uptake, down by about 50 percent but we judged that these peptides were still maintained in translocation activity. Thus, it was known that four amino acids(M, I, I, Y) of the N-terminus of TCTP were necessary in cell penetrating activity.

Figure 6:
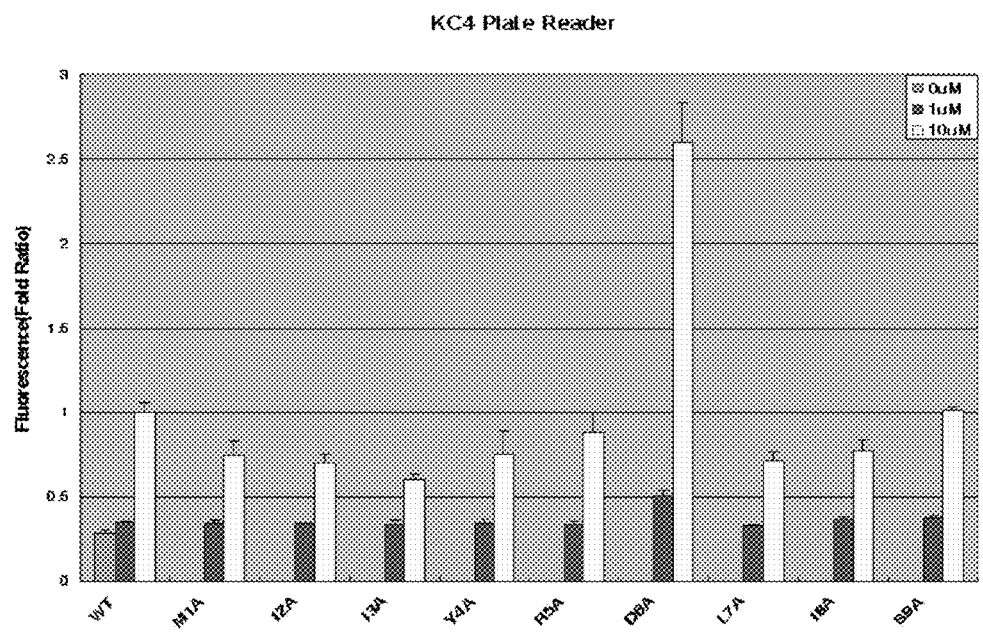
FIG. 6 shows the same result of FIG. 5 at the sensitivity of 100.

Meanwhile, when the sensitivity of KC4 plate reader was set down to 75, we could not analyze the result of cell penetrating activity at relatively low concentration of 1 or 10 μM, so sensitivity of reader was fixed at 100 (FIG. 6). At this time, because fluorescence intensity at 100 μM was very strong, we could not express in a same graph.

As shown in FIG. 6, when fluorescence intensity of TCTP (1-9) at 10 μM was set to be 1, alanine substituent for amino acid residue 6th, aspartic acid of TCTP(1-9)(SEQ ID No.: 13) had 2.5 times higher penetrating activity than natural peptide, TCTP(1-9). Aspartic acid is a amino acid with negative charge and only residue having negative charge of TCTP(1-9). Thus it was considered that amino acid with negative charge decreased the activity of cell penetration of TCTP.

Natural peptides of TCTP(1-10), (1-9), (1-8), (2-10) were efficiently translocated at a high concentration, while these peptides had lower efficiency than control peptide, TAT at a relatively low concentration of 1 μM and 10 μM (EXAMPLE 2). However, from the above results it was shown that analogues of deletion, addition or substitution of 6th residue had a excellent penetrating activity at a low concentration.

From all of the above results, four amino acids(M, I, I, Y) on N-terminus of TCTP played a necessary role in cell penetrating activity and particularly alanine substituent for 6th residue, aspartic acid increased suddenly cell penetrating activity at a low concentration(10 μM). At this time, we assumed that which penetrating activity was increased at a low concentration but decreased at a high concentration was due to low solubility of alanine substituent with hydrophobic property.

[Example 5] Cell Penetrating Activity of Mutant Peptides

As shown in EXAMPLE 4, it was confirmed that substituent peptides of the present invention had a cell membrane penetrating activity. So to identify which mutant forms of the present peptides have penetrating activity, we examined translocation efficiency of mutant peptides.

1) Construction of Mutant Peptides

From the results of EXAMPLE 4, various mutant peptides were constructed with the frame of TCTP (1-10)(SEQ ID No.: 1).

| Classification | Sequence of amino acid | SEQ ID No. |
| --- | --- | --- |
| TCTP-CPP#1 | MIIYRDLISKK | 20 |
| TCTP-CPP#2 | MIIYRDKKSH | 21 |
| TCTP-CPP#3 | MIIFRDLISH | 22 |
| TCTP-CPP#4 | MIISRDLISH | 23 |
| TCTP-CPP#5 | QIISRDLISH | 24 |
| TCTP-CPP#6 | CIISRDLISH | 25 |
| TCTP-CPP#7 | MIIYRALISHKK | 26 |
| TCTP-CPP#8 | MIIYRIAASHKK | 27 |
| TCTP-CPP#9 | MIIRRDLISE | 28 |
| TCTP-CPP#10 | MIIYRAEISH | 29 |
| TCTP-CPP#11 | MIIYARRAEE | 30 |
| TCTP-CPP#12 | MIIFRIAASHKK | 31 |
| TCTP-CPP#13 | MIIFRALISHKK | 32 |
| TCTP-CPP#14 | MIIFRAAASHKK | 33 |
| TCTP-CPP#15 | FIIFRIAASHKK | 34 |
| TCTP-CPP#16 | LIIFRIAASHKK | 35 |
| TCTP-CPP#17 | WIIFRIAASHKK | 36 |
| TCTP-CPP#18 | WIIFRAAASHKK | 37 |
| TCTP-CPP#19 | WIIFRALISHKK | 38 |
| TCTP-CPP#20 | MIIFRIAAYHKK | 39 |
| TCTP-CPP#21 | WIIFRIAAYHKK | 40 |
| TCTP-CPP#22 | MIIFRIAATFIKK | 41 |
| TCTP-CPP#23 | WIIFRIAATHKK | 42 |
| TCTP-CPP#24 | MIIFKIAASHKK | 43 |
| TCTP-CPP#25 | WIIFKIAASHKK | 44 |
| TCTP-CPP#26 | MIIFAIAASHKK | 45 |
| TCTP-CPP#27 | LIIFRILISHKK | 46 |
| TCTP-CPP#28 | MIIFRILISHKK | 47 |
| TCTP-CPP#29 | LIIFRILISHRR | 48 |
| TCTP-CPP#30 | LIIFRILISHHH | 49 |
| TCTP-CPP#31 | LIIFRILISHK | 50 |
| TCTP-CPP#32 | LIIFRILISHR | 51 |
| TCTP-CPP#33 | LIIFRILISH | 52 |
| TCTP-CPP#34 | LIIFAIAASHKK | 53 |
| TCTP-CPP#35 | LIIFAILISHKK | 54 |

N-terminus of each peptide was labeled with fluorescence dye, FITC and C-terminus was protected. Peptide purity (>95%) was determined by HPLC. Synthesis of the peptides of the present invention was requested to PEPTRON, Inc.

2) Cell Culture and Incubation of Peptides

HeLa cell line was propagated in DMEM supplemented with 10% FBS and 100 units/mL penicillin-streptomycin. Cells were grown in a 5% $CO_2$ incubator at 37° C.

Figure 7:
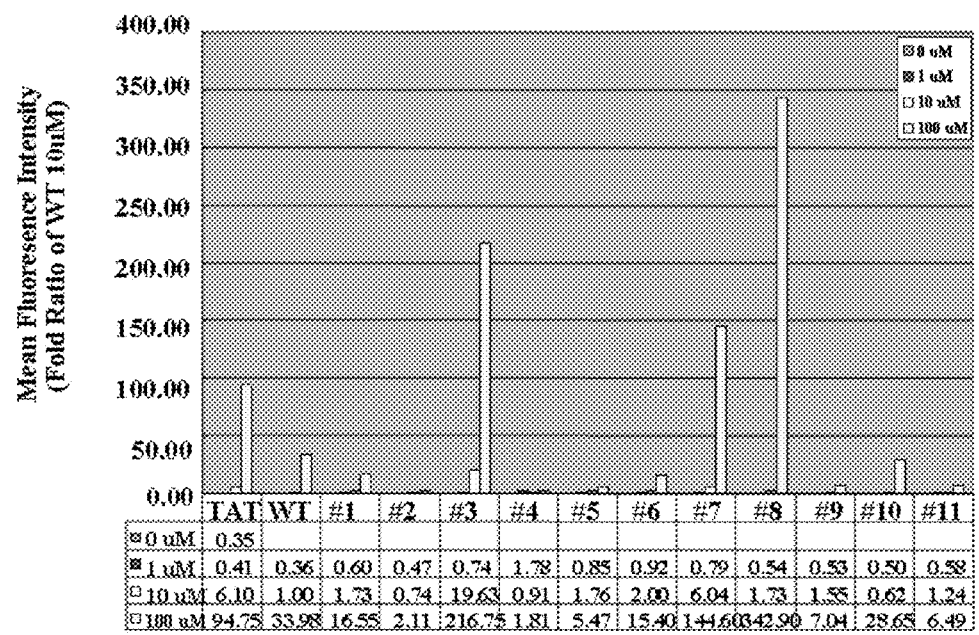
FIG. 7 shows mean fluorescence intensity showing a cellular uptake of mutant peptides of TCTP-derived peptides (#1-11) treated for 2 hours at various concentrations using FACS.
Figure 8:
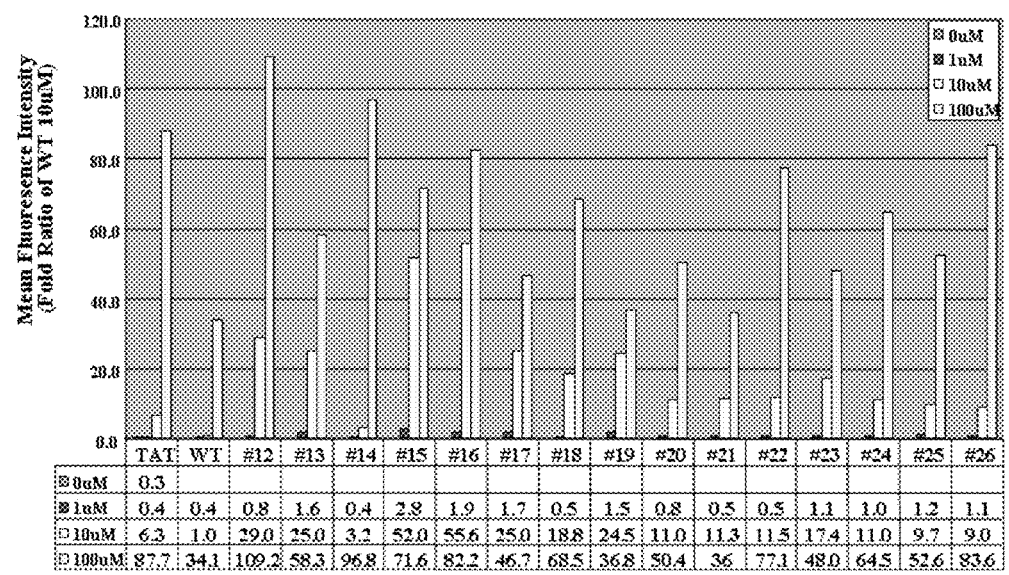
FIG. 8 shows mean fluorescence intensity showing a cellular uptake of mutant peptides of TCTP-derived peptides (#12-26) treated for 2 hours at concentrations using FACS.
Figure 9:
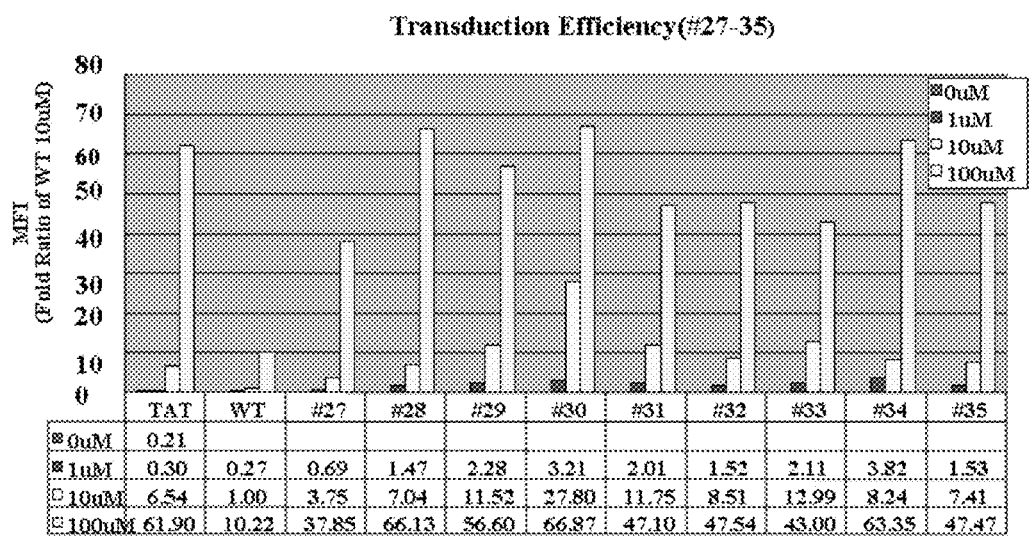
FIG. 9 shows mean fluorescence intensity showing a cellular uptake of mutant peptides of TCTP-derived peptides (#27-35) treated for 2 hours at various concentrations using FACS.

HeLa cells were cultured in 6-well plate until they were 70~80% grown up before a day of the experiment. The cells were washed with DMEM of 37° C. twice, and TCTP-derived peptides synthesized in Example 5-1) were treated to the culture medium in a dose dependent manner (0, 1, 10, 100 μM), then the cells was incubated for 2 hours in an $CO_2$ incubator at 37° C., After the incubation, the cells were washed in cool PBS two times and treated with 1 mg/ml trypsin for 15 min at 37° C. to digest peptides attached on cell membrane and washed in PBS twice again. Then, the cells were analyzed by FACS at emission 510 nm and excitation 530 nm for a measurement of FITC of intracellular uptake marker (FIGS. 7, 8 and 9). Intracellular translocation efficiency of mutant peptides, TCTP-CPP#1-35(SEQ ID Nos.: 20-54) was compared to wild type(WT), TCTP(1-10)(SEQ ID No.: 1) and control peptide, TAT(48-57).

3) Relationship Between Peptide Variants and Cell Penetrating Activity

When mutant peptides were designed, each position of the residues can be substituted with all 20 amino acids like alanine substitution, but this is inefficient to search the best effective mutant out of all peptides because charge and isoelectric point of whole peptide after change of other neighboring position of amino acid also have to be considered. Thus we tried new modification on the basis of the results deduced after primary changes then we designed new variant peptides to verify the role of crucial amino acid. New mutant peptides and sequences were arranged in the table at EXAMPLE 5-1). We intended to explain the mutated position easily by giving a number from 1 to X(from N-terminus) to each ten amino acid of wild type(WT)(SEQ ID No.: 1). To increase the solubility and binding efficiency of WT to cell membrane(in the same reason of use of polyarginine and polylysine), we did the lysine substitution at the position of WT-X and simultaneous addition of lysine at the same position(SEQ ID No.: 20), two lysine substitutions at the position of WT-VII,VIII(SEQ ID No.: 21) and two lysine additions to WT(SEQ ID No.: 26)(SEQ ID No.: 27). Only SEQ ID No.: 26 and SEQ ID No.: 27 of these variants increased cell penetrating activity. According to results comparing and analysing mean fluorescence intensity (MFI) when MFI of WT at the concentration of 10 µM was set to 1, TAT, SEQ ID No.: 26 and SEQ ID NOS.: 27 were 6.1 times, 6.04 times and 1.73 times higher than WT at the concentration of 10 µM, respectively, and TAT, SEQ ID No.: 26 and SEQ ID No.: 27 were 94.75 times, 144.6 times and 342.9 times higher than WT at the concentration of 100 µM in cell penetrating activity, respectively. Therefore variant peptides of all 12 amino acids adding two lysines at C-terminus of WT was maintained in next designed variant peptides(from SEQ ID No.: 31) and substitution with other basic amino acids than lysine and change of number of basic amino acids were tested(SEQ ID Nos.: 48-52). As a result, additions of 1 or 2 basic amino acid at the C-terminus showed higher efficiency than WT.

Figure 11A:
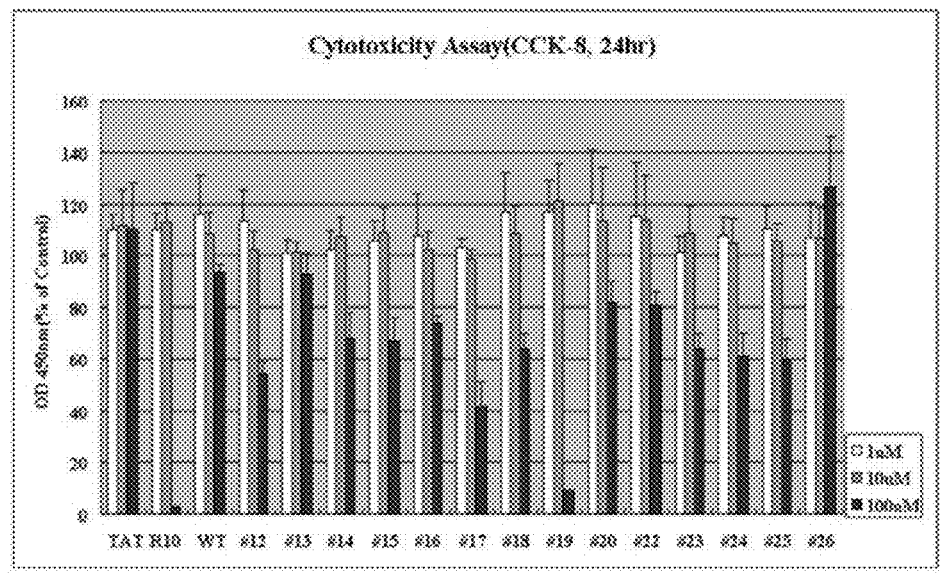
FIG. 11A shows cytotoxicity of mutant peptides of TCTP-derived peptides (#12-26) treated for 24 hours at various concentrations.
Figure 11B:
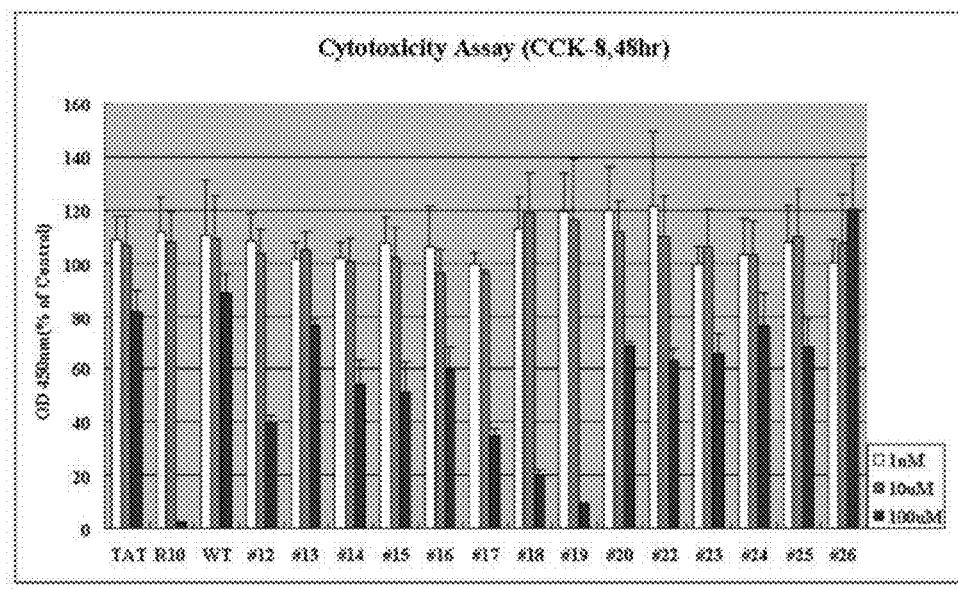
FIG. 11B shows cytotoxicity of mutant peptides of TCTP-derived peptides (#12-26) treated for 48 hours at various concentrations.

To analyze the role of sulfur of methionine in the position of WT-1, we substituted methionine(M) with glutamine(Q) or cysteine(C)(comparison with SEQ ID No.: 23 and SEQ ID Nos.: 24-25). As a result, sulfur didn't play a crucial role and so to test the role of hydrophobicity of methionine, methionine was substituted by phenylalanine(F), leucine(L) or tryptophan(W) (comparison with SEQ ID No.: 31 and SEQ ID No.: 34-36, comparison with SEQ ID No.: 32 and SEQ ID No.: 38, comparison with SEQ ID No.: 33 and SEQ ID No.: 37, comparison with SEQ ID No.: 39 and SEQ ID No.: 40, comparison with SEQ ID No.: 41 and SEQ ID No.: 42, comparison with SEQ ID No.: 43 and SEQ ID No.: 44, comparison with SEQ ID No.: 46 and SEQ ID No.: 47). Consequently, cell penetrating activities of SEQ ID Nos.: 37, 38 and 39 were lower than SEQ ID No.: 34 at the concentration of 100 µM but were 52.0 times, 55.6 times and 25.0 times higher than WT in the concentration of 10 µM, respectively, and so these peptides had an excellent translocation efficiency in comparison with SEQ ID No.: 31(29 times higher than WT). As results of SEQ ID No.: 38 in comparison with SEQ ID No.: 32 and SEQ ID No.: 37 in comparison with SEQ ID No.: 33, substitution for tryptophan did not increase translocation efficiency. This result might be related to cytotoxicity of tryptophan substituents at the concentration of 100 µM(FIG. 11). In comparison between SEQ ID No.: 39 & 40, SEQ ID No.: 41 & 42, SEQ ID No.: 43 & 44, substitution for tryptophan instead of methionine did not induce the important changes in the aspect of efficiency and cytotoxicity. Substitution for phenylalanine(SEQ ID No.: 34) or leucine(SEQ ID No.: 35) brought about the increased result of translocation efficiency at the concentration of 10 µM and a decreased result at 100 µM, compared to SEQ ID No.: 31. Leucine substituents in SEQ ID Nos.: 31, 34, 35 and 36 caused the most increased result at 10 µM and the little decreased result at 100 µM. Cytotoxicity of SEQ ID No.: 35 was weaker than SEQ ID No.: 31 at 100 µM. In SEQ ID No.: 46(3.75 times higher than MFI of WT 10 µM) and SEQ ID No.: 47(7.04 times higher than MFI of WT 10 µM), substitution for leucine caused the decreased penetrating activity but toxicity of SEQ ID No.: 46 was weaker than that of SEQ ID No.: 47. Considering problems of methionine with cytotoxicity and reduction instability, we judged it was most appropriate that methionine was substituted by leucine and so introduced leucine in peptide variants after this experiment (From SEQ ID No.: 48).

To test the role of tyrosine(Y) at the position of WT-IV, by substituting tyrosine with phenylalanine(F) having no hydroxyl group but isostericity like a tyrosine or serine(S) having hydroxyl group like a tyrosine, we tested the importance of hydrophobicity and the action of hydroxyl group and so on in this position. SEQ ID Nos.: 22 and 25 were 19.63 times and 0.91 times higher than WT at 10 µM and 216.75 times and 1.81 times higher at 100 µM, respectively. From this result, it was known that increase of hydrophobicity enhanced cell penetrating activity in this position, and so after this experiment we introduced phenylalanine in the position of WT-IV of peptide variants (From SEQ ID No.: 31).

We compared substituents for basic amino acid by substituting arginine(R) with lysine(comparison between SEQ ID No.: 31 and 43, and between SEQ ID No.: 36 and 44) or alanine(comparison between SEQ ID No.: 31 and 45 and between SEQ ID No.: 35 and 53) in the position of WT-V. As a result, translocation efficiency of SEQ ID No.: 31(26.77 times increase in comparison with WT) was lower than SEQ ID No.: 43(12.1 times increase) and efficiency of SEQ ID No.: 36(18.4 times increase in comparison with WT) was lower than SEQ ID No.: 44(15.04 times increase) at 10 µM. Translocation efficiency of SEQ ID No.: 45(11.47 times increase in comparison with WT) and SEQ ID No.: 53(8.24 times increase in comparison with WT) was lower than SEQ ID No.: 31 and 35(29.53 times increase) at 10 µM. From these results, we thought that maintenance of the arginine at position of WT-V had advantages.

Aspartic acid at the position of WT-VI, because SEQ ID No.: 13 had a good efficiency at the low concentration (EXAMPLE 4), was substituted by alanine or isoleucine to increase hydrophobicity. In comparison between SEQ ID No.: 31(WT-VI:I) and 33(WT-VI:A), translocation efficiencies of both was similarly increased at 100 µM but since increased penetrating activity of SEQ ID No.: 31(29 times increase in comparison with WT) was far better than SEQ ID No.: 33(3.2 times increase in comparison with WT) at 10 µM, isoleucine substitution was more effective than alanine substitution. From these results, after this experiment, isoleucine was introduced at the position of WT-VI of peptide variant (from SEQ ID No.: 31, 34-36, 39).

When leucine and isoleucine at the position of WT-VII and VIII were substituted by alanine respectively(SEQ ID No.: 14 & 15), cell penetrating activity was decreased and when both were substituted by basic amino acids, this activity was decreased twice(in the comparison between SEQ ID No.: 1 and 21) and when only leucine at the position of WT-VII were substituted by glutamic acid(E) having negative charge with strong hydrophilicity, this activity was decreased to same degree with alanine substituent (in the comparison between SEQ ID No.: 1 and 29) and thus it was concluded that most effective amino acids in both positions were leucine and isoleucine.

Serine at the position of WT-IX, when SEQ ID No.: 39(WT-IX:Y) and 41(WT-IX:T) substituted by each tyrosine and threonine only at this position were compare with SEQ ID No.: 31(WT-IX:S) in cell penetrating activity, should be maintained for the best effect. Meanwhile in all case of substitution for tryptophan instead of methionine at the position of WT-1, efficiency of SEQ ID No.: 36(WT-IX:S) was stronger than SEQ ID No.: 40(WT-IX:Y) and SEQ ID No.: 42(WT-IX:T) only at 10 µM.

It was effective to maintain histidine(H) at the position of WT-X. In comparison cell penetrating activity between SEQ ID No.: 1 and 2 (deletion of histidine from SEQ ID No.: 1), SEQ ID No.: 1 was more effective than SEQ ID No.: 2 at the concentration of 50 μM(See FIGS. 2 & 3), and when histidine was substituted by glutamic acid(in comparison with SEQ ID No.: 1 and 28 & 30, See FIGS. 7, 8 & 9), SEQ ID No.: 28 and SEQ ID No.: 30 were similar with WT at 10 μM and decreased 4-5 times at high concentration.

[Example 6] Identification of Cytotoxicity of Mutant Peptides

Figure 10A:
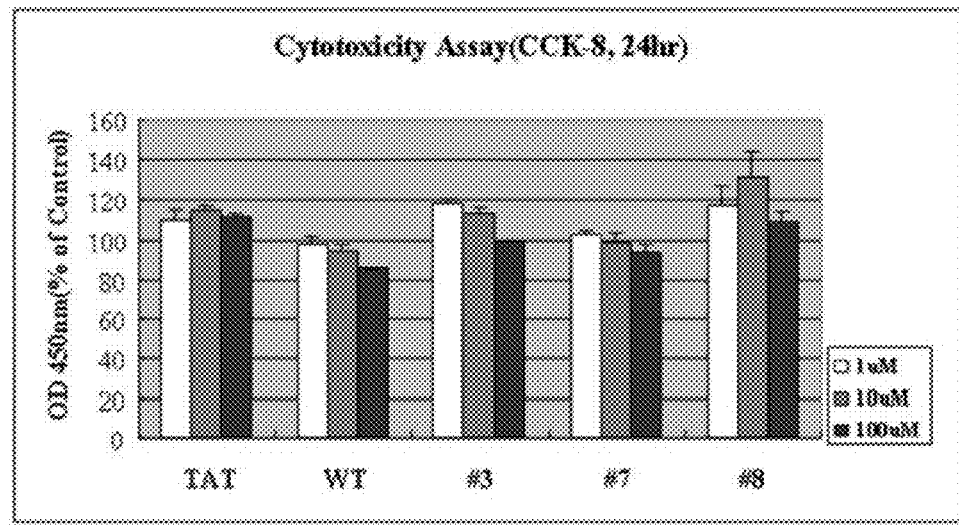
FIG. 10A shows cytotoxicity of mutant peptides of TCTP-derived peptides (#3, #7, #8) treated for 24 hours at a various concentrations.
Figure 10B:
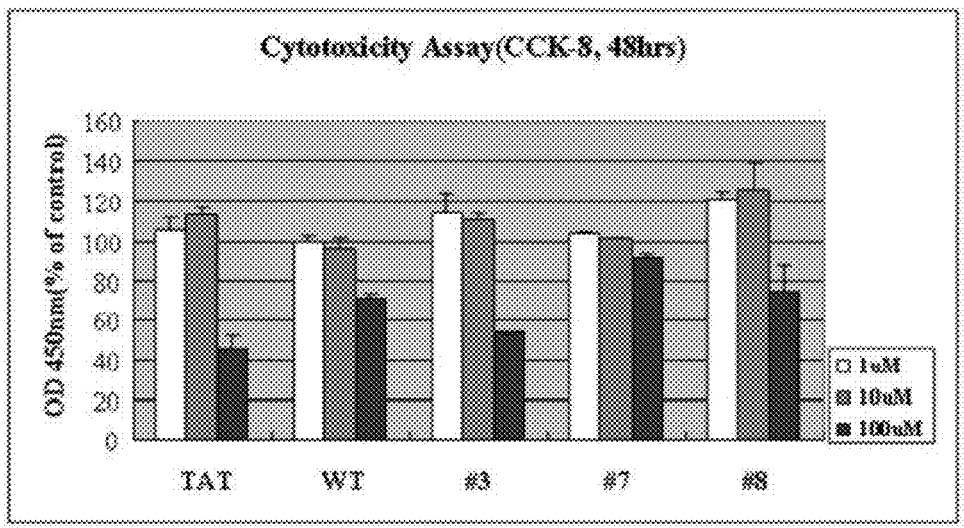
FIG. 10B shows cytotoxicity of mutant peptides of TCTP-derived peptides (#3, #7, #8) treated for 48 hours at various concentrations.
Figure 12A:
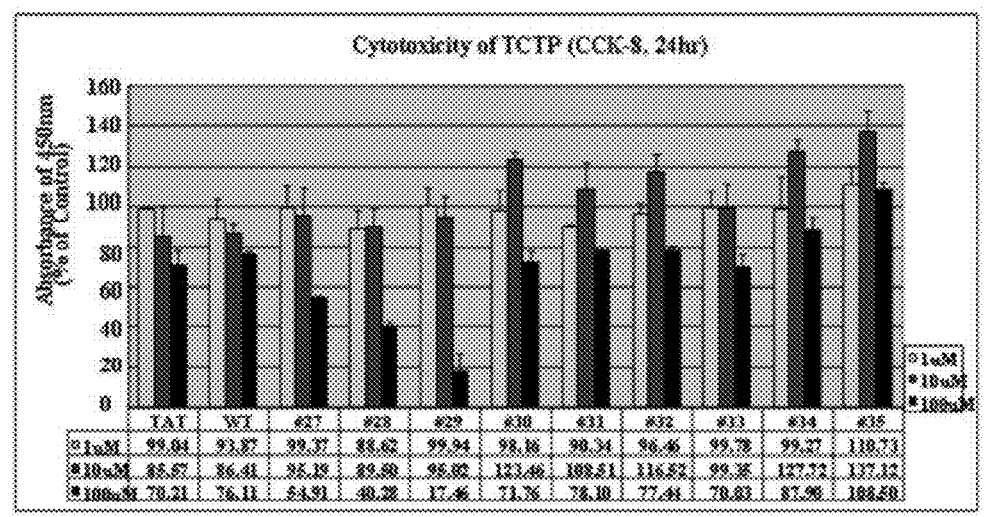
FIG. 12A shows cytotoxicity of mutant peptides of TCTP-derived peptides (#27-35) treated for 24 hours at various concentrations.
Figure 12B:
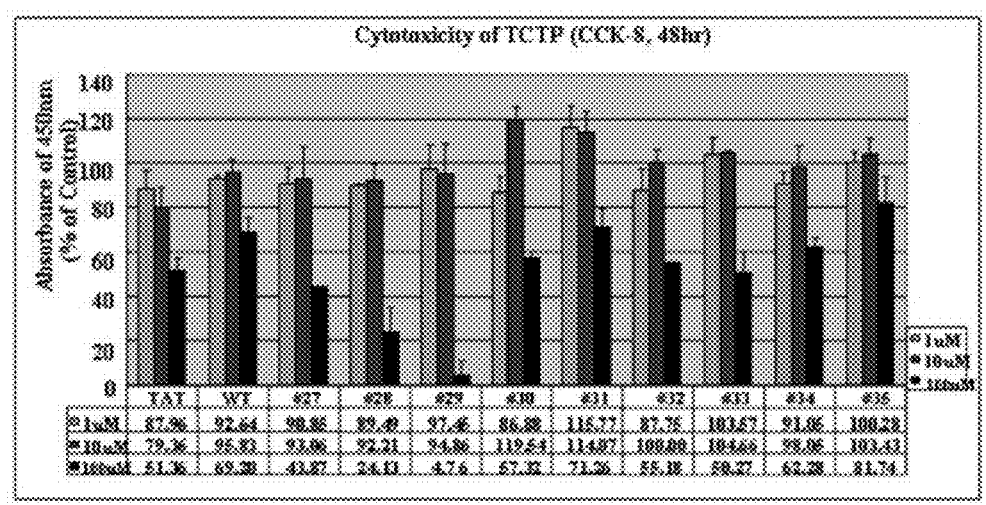
FIG. 12B shows cytotoxicity of mutant peptides of TCTP-derived peptides (#27-35) treated for 48 hours at various concentrations.

To confirm whether cell penetrating activity of the peptides of present invention was due to membrane weakness as a result of cytotoxicity, we measured cytotoxicity as follows. HeLa cells were cultured in 96-well plate until they were 70% grown up before a day of the experiment. Control TAT 48-57 and the mutant peptides at concentrations of 0, 1, 10, 100 μM were treated to DMEM supplemented with 10% FBS for 24 and 48 hours. After 2 hours in addition of 10 μl of CCK-8 to each well, absorbance at 450 nm was measured by KC4 plate reader(FIGS. 10, 11 and 12). As a result of toxicity at 100 μM for 24 hours, cytotoxicity of SEQ ID No.: 1, TCTP(1-10) was about 14% compared with control, and cytotoxicities of the other peptides, TCTP-CPP#3, 7 and 8 were insignificant considering standard deviation. When treated for 48 hours, all peptides had no cytotoxicity at 1 and 10 μM while cytotoxicities of TAT, TCTP(1-10), TCTP-CPP#3, 7 and 8 were about 53.8, 28.3, 46.2, 8.2 and 25.6%, respectively. All of TCTP-CPP#12-26 had no cytotoxicity at 1 μM and 10 μM, but had cytotoxicity beside only TCTP-CPP#26 at 100 μM. Also, all of TCTP-CPP#27-35 had no cytotoxicity at 1 μM and 10 μM but had cytotoxicity at 100 μM.

The invention claimed is:

1. A method for delivering a target substance into a cell, comprising administering a transmembrane complex to a subject, wherein the complex comprises:
   a) a protein transduction domain (PTD) peptide that consists of the sequence of amino acids set forth in any of SEQ ID NOS: 22, 31, 32, 33 and 47; and
   b) a target substance that is linked to the PTD peptide, wherein:
   the target substance is heterologous to the PTD peptide; and
   the PTD peptide is linked to the target substance for delivery of the target substance into the interior of a cell, whereby the target substance is delivered into the cell.

2. The method of claim 1, wherein the target substance is selected from among a nucleic acid, a drug, a chemical compound, a carbohydrate, a lipid, a glycolipid, an enzyme, a regulating factor, a growth factor and an antibody.

3. The method of claim 1, wherein the PTD peptide is linked to the target substance via a linker.

* * * * *

```
                        SEQUENCE LISTING

<160> NUMBER OF SEQ ID NOS: 84

<210> SEQ ID NO 1
    <211> LENGTH: 10
    <212> TYPE: PRT
    <213> ORGANISM: Homo sapiens
    <220> FEATURE:
    <221> NAME/KEY: MISC_FEATURE
    <222> LOCATION: (1)..(10)
    <223> OTHER INFORMATION: 1-10 amino acid residue of TCTP

<400> SEQUENCE: 1

Met Ile Ile Tyr Arg Asp Leu Ile Ser His
    1               5                   10

<210> SEQ ID NO 2
    <211> LENGTH: 9
    <212> TYPE: PRT
    <213> ORGANISM: Homo sapiens
    <220> FEATURE:
    <221> NAME/KEY: MISC_FEATURE
    <222> LOCATION: (1)..(9)
    <223> OTHER INFORMATION: 1-9 amino acid residue of TCTP

<400> SEQUENCE: 2

Met Ile Ile Tyr Arg Asp Leu Ile Ser
    1               5

<210> SEQ ID NO 3
    <211> LENGTH: 8
    <212> TYPE: PRT
    <213> ORGANISM: Homo sapiens
    <220> FEATURE:
    <221> NAME/KEY: MISC_FEATURE
    <222> LOCATION: (1)..(8)
    <223> OTHER INFORMATION: 1-8 amino acid residue of TCTP

<400> SEQUENCE: 3

Met Ile Ile Tyr Arg Asp Leu Ile
    1               5

<210> SEQ ID NO 4
    <211> LENGTH: 9
    <212> TYPE: PRT
    <213> ORGANISM: Homo sapiens
    <220> FEATURE:
    <221> NAME/KEY: MISC_FEATURE
    <222> LOCATION: (1)..(9)
    <223> OTHER INFORMATION: 2-10 amino acid residue of TCTP
```

```
<400> SEQUENCE: 4

Ile Ile Tyr Arg Asp Leu Ile Ser His
1               5

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: 1-7 amino acid residue of TCTP

<400> SEQUENCE: 5

Met Ile Ile Tyr Arg Asp Leu
1               5

<210> SEQ ID NO 6
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: 1-6 amino acid residue of TCTP

<400> SEQUENCE: 6

Met Ile Ile Tyr Arg Asp
1               5

<210> SEQ ID NO 7
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: 3-10 amino acid residue of TCTP

<400> SEQUENCE: 7

Ile Tyr Arg Asp Leu Ile Ser His
1               5

<210> SEQ ID NO 8
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)M1A

<400> SEQUENCE: 8

Ala Ile Ile Tyr Arg Asp Leu Ile Ser
1               5

<210> SEQ ID NO 9
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)I2A
```

```
<400> SEQUENCE: 9

Met Ala Ile Tyr Arg Asp Leu Ile Ser
1               5

<210> SEQ ID NO 10
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)I3A

<400> SEQUENCE: 10

Met Ile Ala Tyr Arg Asp Leu Ile Ser
1               5

<210> SEQ ID NO 11
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)Y4A

<400> SEQUENCE: 11

Met Ile Ile Ala Arg Asp Leu Ile Ser
1               5

<210> SEQ ID NO 12
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)R5A

<400> SEQUENCE: 12

Met Ile Ile Tyr Ala Asp Leu Ile Ser
1               5

<210> SEQ ID NO 13
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)D6A

<400> SEQUENCE: 13

Met Ile Ile Tyr Arg Ala Leu Ile Ser
1               5

<210> SEQ ID NO 14
<211> LENGTH: 9
<212> TYPE: PRT
<213> ORGANISM: Artificial Sequence
```

```
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)L7A

<400> SEQUENCE: 14

Met Ile Ile Tyr Arg Asp Ala Ile Ser
1               5

<210> SEQ ID NO 15
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)I8A

<400> SEQUENCE: 15

Met Ile Ile Tyr Arg Asp Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(9)
<223> OTHER INFORMATION: TCTP(1-9)S9A

<400> SEQUENCE: 16

Met Ile Ile Tyr Arg Asp Leu Ile Ala
1               5

<210> SEQ ID NO 17
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: DNA sequence coding 1-10 amino acid residue of
      TCTP

<400> SEQUENCE: 17
atgattatct accgggacct catcagccac                                    30

<210> SEQ ID NO 18
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: DNA sequence coding 1-9 amino acid residue of
      TCTP

<400> SEQUENCE: 18
atgattatct accgggacct catcagc                                       27

<210> SEQ ID NO 19
<211> LENGTH: 10
```

```
<212> TYPE: PRT
<213> ORGANISM: Human immunodeficiency virus
<220> FEATURE:
<221> NAME/KEY: MISC_FEATURE
<222> LOCATION: (1)..(10)
<223> OTHER INFORMATION: 48-57 amino acid residue of TAT

<400> SEQUENCE: 19

Gly Arg Lys Lys Arg Arg Gln Arg Arg Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(11)
<223> OTHER INFORMATION: TCTP-CPP#1

<400> SEQUENCE: 20

Met Ile Ile Tyr Arg Asp Leu Ile Ser Lys Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#2

<400> SEQUENCE: 21

Met Ile Ile Tyr Arg Asp Lys Lys Ser His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#3

<400> SEQUENCE: 22

Met Ile Ile Phe Arg Asp Leu Ile Ser His
1               5                   10

<210> SEQ ID NO 23
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#4

<400> SEQUENCE: 23

Met Ile Ile Ser Arg Asp Leu Ile Ser His
1               5                   10
```

```
<210> SEQ ID NO 24
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#5

<400> SEQUENCE: 24

Gln Ile Ile Ser Arg Asp Leu Ile Ser His
1               5                   10

<210> SEQ ID NO 25
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#6

<400> SEQUENCE: 25

Cys Ile Ile Ser Arg Asp Leu Ile Ser His
1               5                   10

<210> SEQ ID NO 26
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#7

<400> SEQUENCE: 26

Met Ile Ile Tyr Arg Ala Leu Ile Ser His Lys Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#8

<400> SEQUENCE: 27

Met Ile Ile Tyr Arg Ile Ala Ala Ser His Lys Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
```

```
<223> OTHER INFORMATION: TCTP-CPP#9

<400> SEQUENCE: 28

Met Ile Ile Arg Arg Asp Leu Ile Ser Glu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#10

<400> SEQUENCE: 29

Met Ile Ile Tyr Arg Ala Glu Ile Ser His
1               5                   10

<210> SEQ ID NO 30
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#11

<400> SEQUENCE: 30

Met Ile Ile Tyr Ala Arg Arg Ala Glu Glu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#12

<400> SEQUENCE: 31

Met Ile Ile Phe Arg Ile Ala Ala Ser His Lys Lys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#13

<400> SEQUENCE: 32

Met Ile Ile Phe Arg Ala Leu Ile Ser His Lys Lys
1               5                   10

<210> SEQ ID NO 33
<211> LENGTH: 12
<212> TYPE: PRT
```

```
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#14

<400> SEQUENCE: 33

Met Ile Ile Phe Arg Ala Ala Ala Ser His Lys Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#15

<400> SEQUENCE: 34

Phe Ile Ile Phe Arg Ile Ala Ala Ser His Lys Lys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#16

<400> SEQUENCE: 35

Leu Ile Ile Phe Arg Ile Ala Ala Ser His Lys Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#17

<400> SEQUENCE: 36

Trp Ile Ile Phe Arg Ile Ala Ala Ser His Lys Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#18

<400> SEQUENCE: 37

Trp Ile Ile Phe Arg Ala Ala Ala Ser His Lys Lys
```

```
<210> SEQ ID NO 38
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#19

<400> SEQUENCE: 38

Trp Ile Ile Phe Arg Ala Leu Ile Ser His Lys Lys
1               5                   10

<210> SEQ ID NO 39
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#20

<400> SEQUENCE: 39

Met Ile Ile Phe Arg Ile Ala Ala Tyr His Lys Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#21

<400> SEQUENCE: 40

Trp Ile Ile Phe Arg Ile Ala Ala Tyr His Lys Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#22

<400> SEQUENCE: 41

Met Ile Ile Phe Arg Ile Ala Ala Thr His Lys Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
```

<222> LOCATION: (1)..(12)
<223> OTHER INFORMATION: TCTP-CPP#23

<400> SEQUENCE: 42

Trp Ile Ile Phe Arg Ile Ala Ala Thr His Lys Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#24

<400> SEQUENCE: 43

Met Ile Ile Phe Lys Ile Ala Ala Ser His Lys Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#25

<400> SEQUENCE: 44

Trp Ile Ile Phe Lys Ile Ala Ala Ser His Lys Lys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#26

<400> SEQUENCE: 45

Met Ile Ile Phe Ala Ile Ala Ala Ser His Lys Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#27

<400> SEQUENCE: 46

Leu Ile Ile Phe Arg Ile Leu Ile Ser His Lys Lys
1               5                   10

<210> SEQ ID NO 47
<211> LENGTH: 12

-continued

<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#28

<400> SEQUENCE: 47

Met Ile Ile Phe Arg Ile Leu Ile Ser His Lys Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#29

<400> SEQUENCE: 48

Leu Ile Ile Phe Arg Ile Leu Ile Ser His Arg Arg
1               5                   10

<210> SEQ ID NO 49
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#30

<400> SEQUENCE: 49

Leu Ile Ile Phe Arg Ile Leu Ile Ser His His His
1               5                   10

<210> SEQ ID NO 50
<211> LENGTH: 11
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(11)
<223> OTHER INFORMATION: TCTP-CPP#31

<400> SEQUENCE: 50

Leu Ile Ile Phe Arg Ile Leu Ile Ser His Lys
1               5                   10

<210> SEQ ID NO 51
<211> LENGTH: 11
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(11)
<223> OTHER INFORMATION: TCTP-CPP#32

<400> SEQUENCE: 51

Leu Ile Ile Phe Arg Ile Leu Ile Ser His Arg
1               5                   10

<210> SEQ ID NO 52
<211> LENGTH: 10
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(10)
<223> OTHER INFORMATION: TCTP-CPP#33

<400> SEQUENCE: 52

Leu Ile Ile Phe Arg Ile Leu Ile Ser His
1               5                   10

<210> SEQ ID NO 53
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#34

<400> SEQUENCE: 53

Leu Ile Ile Phe Ala Ile Ala Ala Ser His Lys Lys
1               5                   10

<210> SEQ ID NO 54
<211> LENGTH: 12
<212> TYPE: PRT
<213> ORGANISM: Artificial Sequence
<220> FEATURE:
<223> OTHER INFORMATION: mutant peptide based on human sequence
<220> FEATURE:
<221> NAME/KEY: MISC_FEATURE
<222> LOCATION: (1)..(12)
<223> OTHER INFORMATION: TCTP-CPP#35

<400> SEQUENCE: 54

Leu Ile Ile Phe Ala Ile Leu Ile Ser His Lys Lys
1               5                   10

<210> SEQ ID NO 55
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: DNA sequence coding TCTP-CPP#3

<400> SEQUENCE: 55
atgattattt ttcgcgatct gattagccat                                    30

<210> SEQ ID NO 56
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP CPP#7

<400> SEQUENCE: 56
atgattattt atcgcgcgct gattagccat aaaaaa     36

<210> SEQ ID NO 57
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#8

<400> SEQUENCE: 57
atgattattt atcgcattgc ggcgagccat aaaaaa     36

<210> SEQ ID NO 58
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#12

<400> SEQUENCE: 58
atgattattt ttcgcattgc ggcgagccat aaaaaa     36

<210> SEQ ID NO 59
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#13

<400> SEQUENCE: 59
atgattattt ttcgcgcgct gattagccat aaaaaa     36

<210> SEQ ID NO 60
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#14

<400> SEQUENCE: 60
atgattattt ttcgcgcggc ggcgagccat aaaaaa     36

<210> SEQ ID NO 61
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#15

<400> SEQUENCE: 61
tttattattt ttcgcattgc ggcgagccat aaaaaa     36

<210> SEQ ID NO 62
<211> LENGTH: 36
<212> TYPE: DNA
<213> ORGANISM: Homo sapiens
<220> FEATURE:

<221> NAME/KEY: misc_feature
<222> LOCATION: (1)..(36)
<223> OTHER INFORMATION: DNA sequence coding TCTP-CPP#16

<400> SEQUENCE: 62
ctgattattt ttcgcattgc ggcgagccat aaaaaa        36

<210> SEQ ID NO 63
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#17

<400> SEQUENCE: 63
tggattattt ttcgcattgc ggcgagccat aaaaaa        36

<210> SEQ ID NO 64
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#18

<400> SEQUENCE: 64
tggattattt ttcgcgcggc ggcgagccat aaaaaa        36

<210> SEQ ID NO 65
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#19

<400> SEQUENCE: 65
tggattattt ttcgcgcgct gattagccat aaaaaa        36

<210> SEQ ID NO 66
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#20

<400> SEQUENCE: 66
atgattattt ttcgcattgc ggcgtatcat aaaaaa        36

<210> SEQ ID NO 67
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#21

<400> SEQUENCE: 67
tggattattt ttcgcattgc ggcgtatcat aaaaaa        36

```
<210> SEQ ID NO 68
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#22

<400> SEQUENCE: 68
atgattattt ttcgcattgc ggcgacccat aaaaaa                           36

<210> SEQ ID NO 69
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#23

<400> SEQUENCE: 69
tggattattt ttcgcattgc ggcgacccat aaaaaa                           36

<210> SEQ ID NO 70
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#24

<400> SEQUENCE: 70
atgattattt ttaaaattgc ggcgagccat aaaaaa                           36

<210> SEQ ID NO 71
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#25

<400> SEQUENCE: 71
tggattattt ttaaaattgc ggcgagccat aaaaaa                           36

<210> SEQ ID NO 72
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#26

<400> SEQUENCE: 72
atgattattt ttgcgattgc ggcgagccat aaaaaa                           36

<210> SEQ ID NO 73
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#27
```

```
<400> SEQUENCE: 73
ctgattattt ttcgcattct gattagccat aaaaaa                              36

<210> SEQ ID NO 74
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#28

<400> SEQUENCE: 74
atgattattt ttcgcattct gattagccat aaaaaa                              36

<210> SEQ ID NO 75
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#29

<400> SEQUENCE: 75
ctgattattt ttcgcattct gattagccat cgccgc                              36

<210> SEQ ID NO 76
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#30

<400> SEQUENCE: 76
ctgattattt ttcgcattct gattagccat catcat                              36

<210> SEQ ID NO 77
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: DNA sequence coding TCTP-CPP#31

<400> SEQUENCE: 77
ctgattattt ttcgcattct gattagccat aaa                                 33

<210> SEQ ID NO 78
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: DNA sequence coding TCTP-CPP#32

<400> SEQUENCE: 78
ctgattattt ttcgcattct gattagccat cgc                                 33

<210> SEQ ID NO 79
<211> LENGTH: 30
<212> TYPE: DNA
<213> ORGANISM: Homo sapiens
```

```
<220> FEATURE:
<221> NAME/KEY: misc_feature
<222> LOCATION: (1)..(30)
<223> OTHER INFORMATION: DNA sequence coding TCTP-CPP#33

<400> SEQUENCE: 79
ctgattattt ttcgcattct gattagccat                                       30

<210> SEQ ID NO 80
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#34

<400> SEQUENCE: 80
ctgattattt ttgcgattgc ggcgagccat aaaaaa                                36

<210> SEQ ID NO 81
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: DNA sequence coding TCTP-CPP#35

<400> SEQUENCE: 81
ctgattattt ttgcgattct gattagccat aaaaaa                                36

<210> SEQ ID NO 82
<211> LENGTH: 11
<212> TYPE: PRT
<213> ORGANISM: Human immunodeficiency virus

<400> SEQUENCE: 82

Tyr Gly Arg Lys Lys Arg Arg Gln Arg Arg Arg
1               5                   10

<210> SEQ ID NO 83
<211> LENGTH: 34
<212> TYPE: PRT
<213> ORGANISM: herpes simplex virus 1

<400> SEQUENCE: 83

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 84
<211> LENGTH: 16
<212> TYPE: PRT
<213> ORGANISM: Drosophila melanogaster

<400> SEQUENCE: 84

Arg Gln Ile Lys Ile Trp Phe Gln Asn Arg Arg Met Lys Trp Lys Lys
1               5                   10                  15
```